(12) United States Patent
Ruiz et al.

(10) Patent No.: US 10,759,138 B2
(45) Date of Patent: Sep. 1, 2020

(54) MOISTURE PERMEABLE HYDROGEL COMPOSITE MATERIALS

(71) Applicant: UNIVERSITY OF PITTSBURGH—OF THE COMMONWEALTH SYSTEM OF HIGHER EDUCATION, Pittsburgh, PA (US)

(72) Inventors: Esteban Ruiz, Pittsburgh, PA (US); David M. Brienza, Pittsburgh, PA (US)

(73) Assignee: University of Pittsburgh - Of The Commonwealth System of Higher Education, Pittsburgh, PA (US)

(*) Notice: Subject to any disclaimer, the term of this patent is extended or adjusted under 35 U.S.C. 154(b) by 60 days.

(21) Appl. No.: 15/766,591

(22) PCT Filed: Oct. 6, 2016

(86) PCT No.: PCT/US2016/055853
§ 371 (c)(1),
(2) Date: Apr. 6, 2018

(87) PCT Pub. No.: WO2017/062690
PCT Pub. Date: Apr. 13, 2017

(65) Prior Publication Data
US 2018/0281340 A1    Oct. 4, 2018

Related U.S. Application Data

(60) Provisional application No. 62/238,051, filed on Oct. 6, 2015.

(51) Int. Cl.
*A61F 2/78* (2006.01)
*A61F 2/80* (2006.01)
(Continued)

(52) U.S. Cl.
CPC .............. *B32B 3/12* (2013.01); *A61F 2/7812* (2013.01); *A61F 2/80* (2013.01); *B32B 3/06* (2013.01);
(Continued)

(58) Field of Classification Search
CPC ............. A61F 2/78; A61F 2/7812; A61F 2/80
See application file for complete search history.

(56) References Cited

U.S. PATENT DOCUMENTS 6,706,364 B2    3/2004    Janusson et al.
2002/0032485 A1    3/2002    Flam et al.
(Continued)

OTHER PUBLICATIONS

Form PCT/ISA/220, PCT Notification of Transmittal of the International Search Report and the Written Opinion of the International Searching Authority, or the Declaration, PCT/US2016/055853, dated Jan. 11, 2017.
(Continued)

*Primary Examiner* — Bruce E Snow
(74) *Attorney, Agent, or Firm* — Paul D. Bangor, Jr., Esq.; Clark Hill, PLC

(57) ABSTRACT

A moisture permeable composite material for a wide variety of applications including without limitation prosthetic liners, orthotic liners, clothing, space suits and environmental suits comprising: an inner layer comprising a hydrogel, or a thin tough hydrogel membrane, or dual network hydrogel; and an outer layer comprising a porous elastomer or an open cell foam.

3 Claims, 14 Drawing Sheets

(51) Int. Cl.
    *B32B 3/12*     (2006.01)
    *B32B 5/18*     (2006.01)
    *B32B 5/24*     (2006.01)
    *B32B 27/28*     (2006.01)
    *B32B 3/26*     (2006.01)
    *B32B 25/10*     (2006.01)
    *B32B 27/08*     (2006.01)
    *B32B 25/08*     (2006.01)
    *B32B 3/08*     (2006.01)
    *B32B 3/28*     (2006.01)
    *B32B 27/12*     (2006.01)
    *B32B 5/26*     (2006.01)
    *B32B 25/04*     (2006.01)
    *B32B 27/06*     (2006.01)
    *B32B 3/06*     (2006.01)
    *B32B 27/18*     (2006.01)
    *B32B 33/00*     (2006.01)
(52) U.S. Cl.
    CPC ............... *B32B 3/08* (2013.01); *B32B 3/266* (2013.01); *B32B 3/28* (2013.01); *B32B 5/18* (2013.01); *B32B 5/245* (2013.01); *B32B 5/26* (2013.01); *B32B 25/04* (2013.01); *B32B 25/08* (2013.01); *B32B 25/10* (2013.01); *B32B 27/065* (2013.01); *B32B 27/08* (2013.01); *B32B 27/12* (2013.01); *B32B 27/18* (2013.01); *B32B 27/283* (2013.01); *B32B 33/00* (2013.01); *A61F 2002/807* (2013.01); *B32B 2250/03* (2013.01); *B32B 2250/04* (2013.01); *B32B 2255/00* (2013.01); *B32B 2255/02* (2013.01); *B32B 2255/10* (2013.01); *B32B 2255/26* (2013.01); *B32B 2260/021* (2013.01); *B32B 2260/048* (2013.01); *B32B 2262/0261* (2013.01); *B32B 2264/102* (2013.01); *B32B 2266/06* (2013.01); *B32B 2266/122* (2016.11); *B32B 2305/022* (2013.01); *B32B 2305/026* (2013.01); *B32B 2305/08* (2013.01); *B32B 2305/72* (2013.01); *B32B 2307/30* (2013.01); *B32B 2307/50* (2013.01); *B32B 2307/54* (2013.01); *B32B 2307/724* (2013.01); *B32B 2307/726* (2013.01); *B32B 2307/728* (2013.01); *B32B 2307/73* (2013.01); *B32B 2307/732* (2013.01); *B32B 2437/00* (2013.01); *B32B 2535/00* (2013.01)

(56) References Cited

U.S. PATENT DOCUMENTS

| | | |
|---|---|---|
| 2004/0181290 A1 | 9/2004 | Caspers |
| 2011/0035027 A1* | 2/2011 | McCarthy ................. A61F 2/80 623/34 |
| 2012/0282584 A1 | 11/2012 | Millon et al. |
| 2013/0035770 A1* | 2/2013 | Egilsson ............... A61F 2/7812 623/36 |
| 2015/0238754 A1 | 8/2015 | Loudin et al. |

OTHER PUBLICATIONS

Form PCT/ISA/210, PCT International Search Report for International Application No. PCT/US2016/055853, dated Jan. 11, 2017.
Form PCT/ISA/237, PCT Written Opinion of the International Searching Authority for International Application No. PCT/US2016/055853, dated Jan. 11, 2017.
Form PCT/IB/326, PCT Notification Concerning Transmittal of International Preliminary Report on Patentability, PCT/US2016/055853, dated Apr. 19, 2018.
Form PCT/IB/373, PCT International Preliminary Report on Patentability for International Application No. PCT/US2016/055853, dated Apr. 19, 2018.

\* cited by examiner

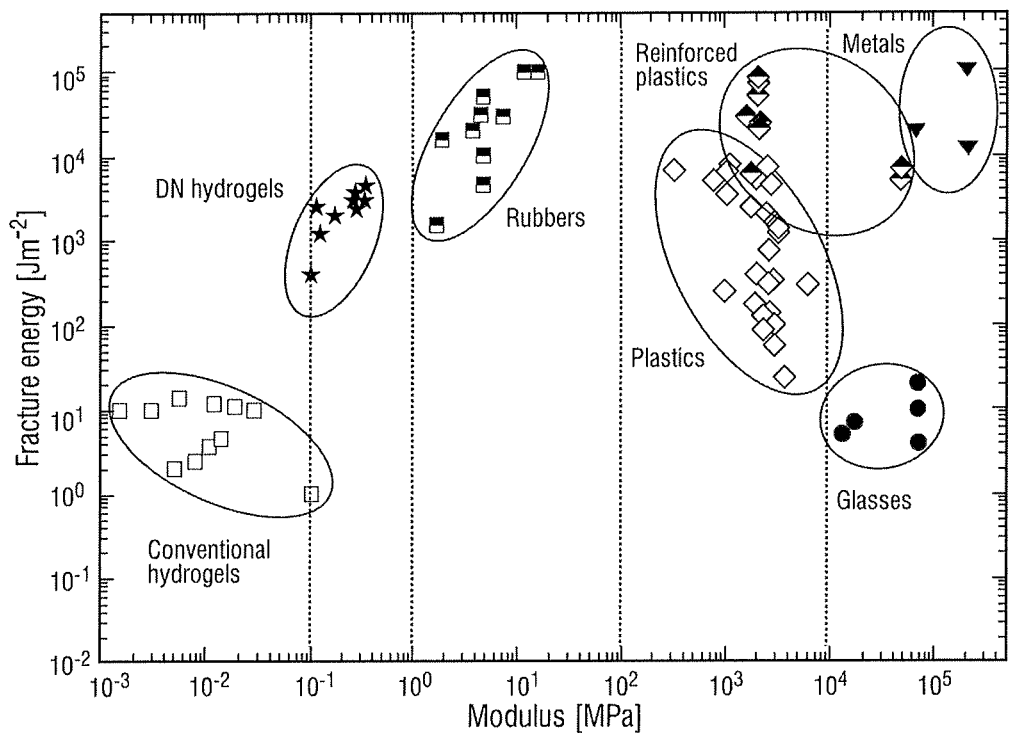
*Fig.1*
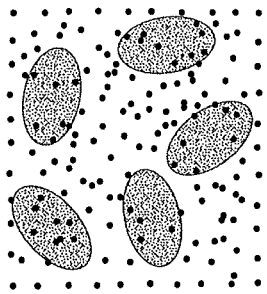 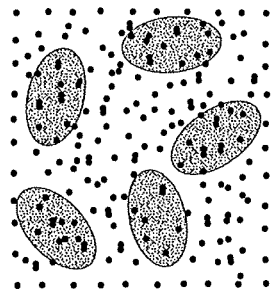
*Fig.2A*      *Fig.2B*
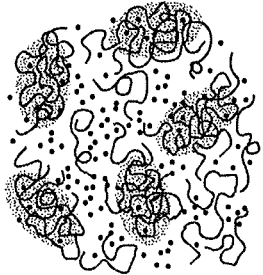 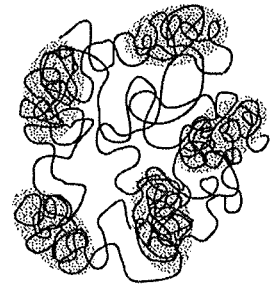
*Fig.2C*      *Fig.2D*

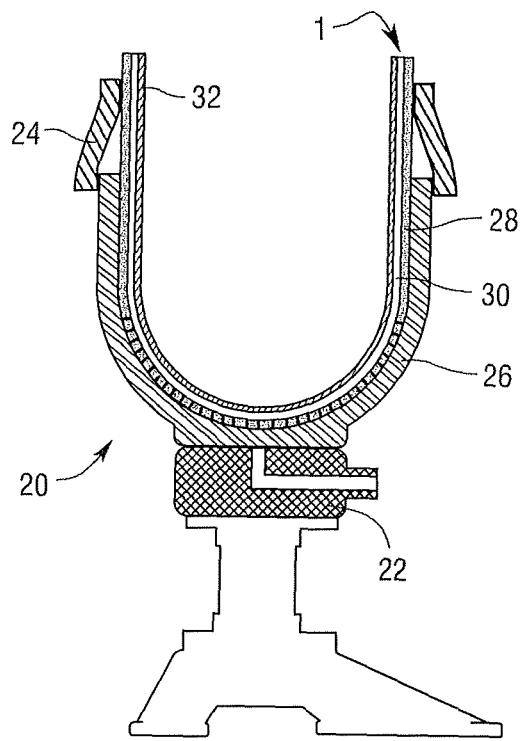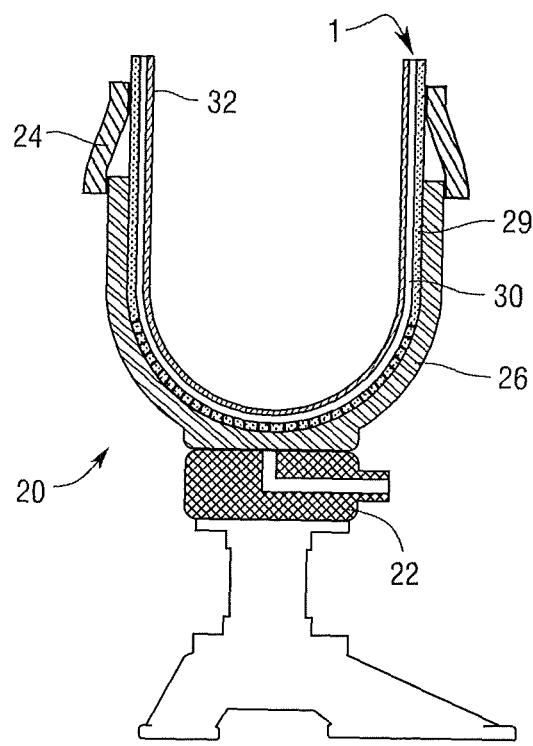
Fig.6    Fig.7
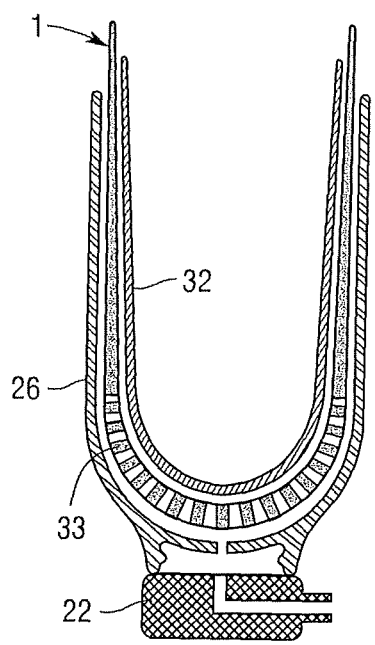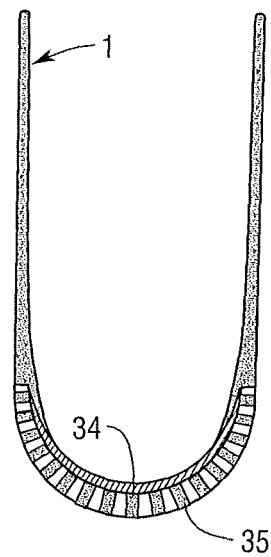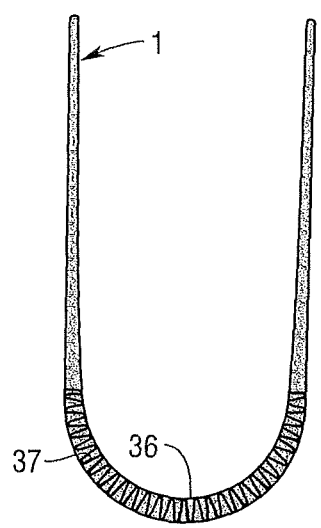
Fig.8    Fig.9    Fig.10

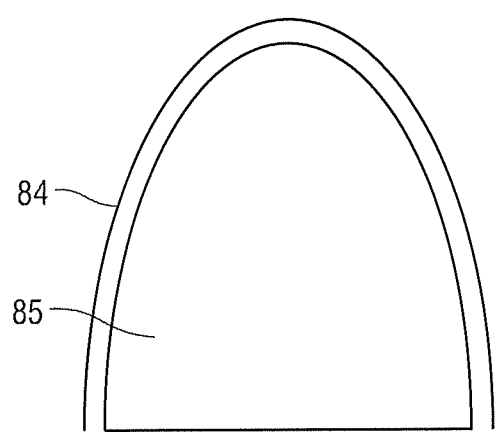
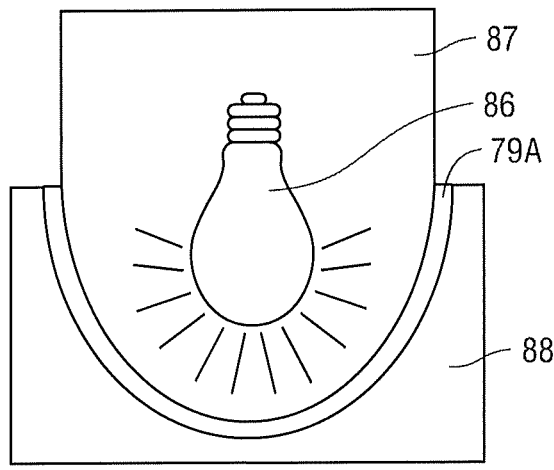
Fig.21A  Fig.21B
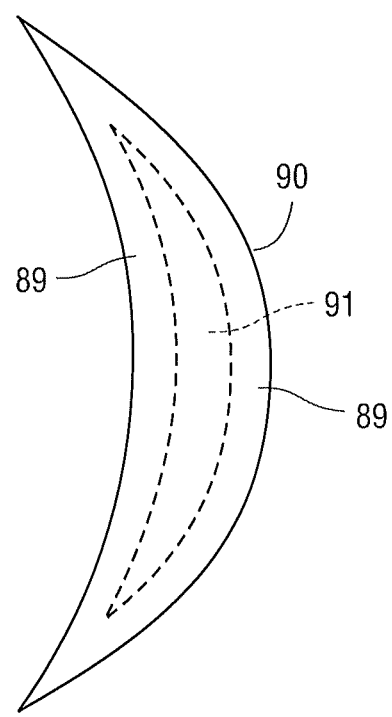
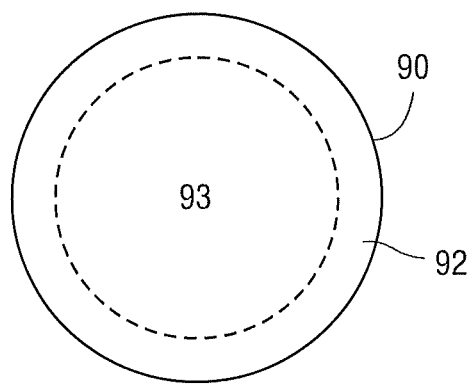
Fig.22A  Fig.22B

MOISTURE PERMEABLE HYDROGEL COMPOSITE MATERIALS

CROSS REFERENCE TO RELATED APPLICATIONS

This application claims the benefit of the filing date of U.S. provisional patent application Ser. No. 62/238,051, filed on Oct. 6, 2015, the entirety of which is incorporated herein by reference for all purposes.

TECHNICAL FIELD

The present disclosure generally relates to moisture permeable hydrogel composite materials for use in a wide variety of applications including without limitation prosthetic liners, orthotic liners, clothing, space suits and environmental suits.

BACKGROUND

One of the most exciting, and rapidly developing areas within rehabilitation science is the development of advanced prosthetics. In many areas prosthetic limbs are advancing rapidly. New rigid yet lightweight materials such as carbon fiber are being borrowed from the aerospace industry to create high performance feet and legs for amputees (there are currently about 1.6 million amputees in the USA and 3.6 million projected by 2050 wishing to return to an active lifestyle which includes running. At the same time microprocessors and miniaturized electronics are being borrowed from the field of robotics to create artificial joints capable of automatically adapting to a user's walking style and speed.

Despite these advances one of the most critical aspects of prosthetics has yet to be similarly revolutionized. The union of the artificial limb to the soft tissue of the residual limb is known as the soft tissue interface of the prosthetic limb. Currently the most prevalent method of interfacing the prosthetic and the residual limb is by using what is known as a prosthetic socket liner. The prosthetic socket liner is a tight fitting 3-9 mm thick sleeve placed over the limb. It is made of a stretchy polymer such as silicone, polyurethane, or thermoplastic elastomer. These materials are selected because they are relatively inert, they are able to stretch to conform to the shape of the limb, and cushion the limb against the hard surface of the prosthetic socket which is typically made of laminated plastic or carbon fiber. Another role of the liner besides cushioning is to provide effective linkage of the prosthetic to the limb. In order to provide this linkage the liner must be air tight. No existing liners are moisture permeable.

A recurring and persistent problem with current liners is the problem of accumulation of excess moisture in the prosthetic limb. Thus it would be desirable to develop a laminar composite material to enhance the function of existing prosthetic liners by allowing for moisture to pass through it while maintaining an air tight seal.

It would also be desirable to create a socket liner which allows sweat to steadily pass through it for removal from the socket of the prosthetic limb. In a preferred embodiment, one or more parts of the liner will comprise water permeable and/or absorbable materials, which can be cleaned and replaced, or else would allow the user to wear the prosthesis continually without removing it.

A preferred enabling technology of the present disclosure will be the use of an advanced biologically compatible tough hydro-gel composite material which interfaces with the soft tissue of the residual limb.

Major findings from: "Hygiene Problems of Residual Limb and Silicone Liners in Transtibial Amputees Wearing the Total Surface Bearing Socket, 2001": Forty-seven percent of the subjects complained of excessive perspiration—the level of perspiration being directly related to the number of hours of TSB use, Although an antiperspirant may be temporarily effective, materials for the socket and liner that allow ventilation of the air and a means to radiate heat from the inside of the silicone liner need to be developed.

Eruption and itching on the residual limb, respectively, maybe caused by perspiration and exfoliated outer layers of skin, powder, and deodorant residues, or allergic reactions induced by the materials used in the silicone liner. The odor from the silicone liner, which was noted in 43.4% of the subjects, may also derive from perspiration and dirt.

Excessive heat and moisture retention within the socket are common complaints of lower limb amputees.

The environment between the liner and skin is perfect for forming a host of residual limb skin problems including contact dermatitis, hyperhydrosis, and bacterial infections.

The prevalence of skin problems of the stump in lower limb amputees was estimated as 36%. Skin problems result in a reduction in walking distance without a break and a reduction in prosthesis use.

Moisture and Temperature have been Implicated in Skin Issues:

Hyperhidrosis

Because of the inability of sweat to evaporate (decrease of transport of sweat) and the increased production of sweat because of the cooling reflex of the skin, this isolation will lead to stasis of sweat in the isolated area. As a consequence, hyperhidrosis (an unbalance between production and evacuation of sweat) will occur. Hyperhidrosis can worsen skin problems of the stump, or can be an initiating or supporting factor in the development of skin problems on amputation stumps as mentioned earlier.

Infections

Infections of the skin that occur on other parts of the body can also occur on the stump, such as folliculitis and furuncles. Most types of prostheses involve prolonged contact with the stump, or at least the distal part of the stump, thereby increasing the humidity of the stump socket environment and making it an excellent culture medium for microorganisms such as bacteria, yeasts and mycoses Infections of the skin of the stump caused by microorganisms are therefore common, but are seldom described in detail in the literature as case reports.

Allergic Contact Dermatitis

Friction, sustained pressure and humidity of the amputation stump may not only act as cofactors to increase the chance of allergic contact dermatitis but may also be primary factors in causing irritant contact dermatitis.

Several known approaches for improving prosthetic liners include Ottobock which has a series of antimicrobial polymer liners which are bioactive. They use silver to reduce microbial activity that extends beyond the simple bioinert standard for prosthetic liners. They call it Silvershield®. It uses a measured slow release of ions from the socket into the liner environment to counter act microorganisms.

The Unity system by Charles King is a mechanical device designed to remove moisture via excess pumps, tubes and solenoids. This sort of solution introduces many more points of failure into the device. It makes the device heavier and requires re-training of care givers in the design and manufacture of the product and retraining of end users in its use.

A bioengineering approach to solving problems associated with prosthetic liners are preferred because there is already a system you can put the product into. Active cooling or active moisture reducing systems are not preferred because they are bulky and would take up valuable space and weight away from the overall prosthetic design space. Microprocessor knee joints and ankles will take precedence over active cooling systems. Addition of bulky hardware increases the unique part count and possibility of user error. In addition it adds to the overall weight, and may require a redesign of existing pylons or knee or ankle joints. So it's preferable to design a liner material which can solve many of the problems already existing without the need for developing a new system support paradigm as would be needed in the case of bulky active cooling systems.

By altering the material properties of the liner, it is possible to deliver the same effects of a larger bulkier system with a minimal increase in size and weight of the existing prosthesis. The material science research around prosthetic liners has centered largely on the mechanical properties of the liners. Liner performance is not judged by the mechanical properties of the liners alone however. Aside from cushioning the limb against pressure and shear, the liner also has to have the role of providing a safe micro environment as well. The micro environment, defined here to be the combination of temperature, moisture and ions, plays an important role in creating a biocompatible and successful prosthesis as much as the macro scale mechanical properties as can be seen by examining the rates of patient reported skin problems and satisfaction.

There are a number of technologies which claim to reduce moisture and temperature for prosthetic liners and the like.

Bonded composites have been used in socket liners. These composites are mostly cloth materials bonded to the polymer liners. The cloth provides structural resilience to the liners.

Macro Scale Polymer Suspension Composites

More complex polymer composites including suspensions have also been proposed, such as a liner comprising a suspension of cork granules in silicone as disclosed in U.S. Patent Publ. No, US20120110713. The idea is that the composite material will feature advanced material properties due to the two materials which make it up. This composite is supposed to act as a means of reducing temperature. However, cork is filled with air, which makes it an excellent insulator of heat. Thus, this will not likely work as intended to reduce excess temperature in the socket of the prosthesis.

Micro Scale Polymer Suspension Composites

Ossur has also made a composite liner material comprising air filled microspheres that are imbedded within the silicone liner material which is itself bonded to a nylon fabric. Microspheres introduce air into the polymer, altering its properties. Ossur does not disclose the specific use of the microspheres which may be for thermal or mechanical properties. The focus of Ossur is to protect the elastic material itself. This is an example of an existing product where the silicone used to make the liner has itself been altered by the addition of small additives. The liner does feature a simple, common laminar composite design but it is not the focus of the patent. See EP patent No. 1263358 B1.

Bonded Polymer Laminate Composites

Ossur also makes use of a laminated composite of silicones of varying durometer values. "A stiffer outer layer of DermoSil® silicone provides outstanding stability, while a softer DermoGel® inner layer nurtures the skin and provides shock absorption and comfort." These liners are currently commercially available. http://www.ossur.com/pages/13399# double-durometer Advanced Material Configuration Composite Liners Another patent by Ossur, U.S. Pat. No. 8,308,817, discloses a prosthetic liner composite material that does not use hydrogels but that has a closed distal end, an open proximal end, an outer surface, and an opposite inner surface, the liner for use in prosthetic and orthopedic devices and comprising: a frictional layer formed from a hydrophobic elastomer material and located along the entirety of the inner surface of the liner, the frictional layer defining a plurality of apertures located along the inner surface, the material of the frictional layer having skin tackiness properties; a porous polymer foam layer in communication with the inner surface and directly laminated to the frictional layer, the porous polymer foam layer is a three-dimensional woven synthetic material including discrete portions of a moisture-absorbing material, the apertures of the frictional layer permitting a transfer of air from the inner surface to the porous polymer foam layer; and a cushioning base layer adhered to the porous polymer foam layer and having greater rigidity than the porous polymer foam layer, the base layer forms a liquid and vapor impervious outer surface of the liner; wherein the porous polymer foam layer is a continuous layer extending between the proximal and distal ends of the liner with the base layer extending over the length of the porous polymer foam layer, the porous polymer foam layer permitting a transfer of air from the inner surface of the liner through a thickness of the porous polymer foam layer and out from the proximal end of the liner, wherein the base layer is close-ended at the distal end of the liner, and defines a close-ended conical shape, and wherein the base layer conforms to the shape of the porous polymer foam layer, wherein the base layer is laminated onto the porous polymer foam layer, thereby the frictional layer, the porous polymer foam layer, and the base layer forming a tri-layered laminate structure.

U.S. Pat. No. 6,974,484 discloses a system for removing perspiration from a residual limb inserted in a prosthesis comprising: a nonporous prosthesis socket; a porous thin sheath adjacent the socket; a nonporous liner adjacent the sheath; an osmotic membrane adjacent the liner that purports to allow water vapor to pass from the limb but preventing liquid from passing to the limb; a nonporous seal that prevents air leakage between the residual limb and the socket; and a vacuum source to reduce the pressure in a space between the limb and socket. U.S. Pat. No. 6,974,484 discloses the following materials (but not hydrogels) for the osmotic membrane: Sympatex hydrophylic polyester block copolymer from Sympatex Technologies, One Merrill Industrial Drive, Suite 201, Hampton, N.H. 03842; the Goretex® material from A.W. Gore & Associates, www.gore.com; the Gill 02 Fabric from Gill North America, 1025 Parkway Industrial Park, Buford, Ga. 30581; and the SealSkinz product from Porvair, Estuary Road, King's Lynn, Norfolk, PE30 2HS, United Kingdom. U.S. Pat. No. 6,974,484 claims to use a negative pressure vacuum applied to the socket to provide the pressure gradient needed to drive moisture dissipation away from the limb through and/or around a nonporous liner adjacent the sheath and an osmotic membrane adjacent the liner. However, it is unlikely to work as described. The mechanism it proposes is to use the vacuum to create negative pressure to vaporize the water on the skin, and to draw out the vapor through the osmotic membrane. The pores are of the size such that individual gaseous molecules of water may pass through them but water droplets, being larger in diameter than the pore cannot. This approach is infeasible since the pressure required to vaporize any moisture on the skin would require the skin to be subjected directly to an elevated vacuum thereby weakening the skin and making it vulnerable to skin irritation.

performance. One would then expect that their material properties differ. However, only two reports comparing elastomeric liner material properties have been published:

1. Covey S J, Muonio, J, Street G M. Flow constraint and loading rate effects on prosthetic liner material and human tissue mechanical response. J Prosthet Ortho. 2000; 12:15-32.

2. Emrich R, Slater K. Comparative analysis of below-knee prosthetic socket liner materials. J Med Eng Technol. 1998; 22:94-98.

TABLE 1

Liners tested. Thickness values reflect those of 10 samples used for compression testing.
Table 1.
Liners tested. Thickness values reflect those of 10 samples used for compression testing.

| Company (Location) | Product | Material* | Mean Thickness (SD) (mm) |
|---|---|---|---|
| ALPS: St, Petersberg. Florida | EasyLiner ELDT 32-3 | Silicone gel w/fabric backing | 4.49 (0.03) |
| | EasyLiner ELDT 32-6 | Silicone gel w/fabric backing | 5.60 (0.00) |
| | EasyLiner Super Stretch ELPX32 | Silicone gel | 6.12 (0.05) |
| | Clearpro SSA44 | Silicone elastomer | 2.06 (0.05) |
| Engineered Silicone Products: Parsippany New Jersey | AEGIS | Silicone elastomer | 2.19 (0.06) |
| | AEGIS Z | Silicone elastomer w/fabric backing | 5.10 (0.00) |
| Fillauer. Inc.: Chattanooga. Tennessee | Silicone Suspension Liner | Silicone elastomer | 2.01 (0.03) |
| Ohio Willow Wood: Mt. Sterling. Ohio | Alpha Liner | Silicone gel w/fabric backing | 9.42 (0.09) (front) |
| Ossur USA, Inc.: Columbia, Maryland | DERMO Liner-9 | Gel silicone† w/fabric backing | 9.29 (0.19) |
| | DERMO Liner-6 | Gel silicone† w/fabric backing | 5.81 (0.15) |
| | Iceross Two Color | Silicone elastomer (two layers) | 2.27 (0.05) |
| | Iceross Comfort, Uniform | Silicone elastomer w/fabric backing | 5.89 (0.09) |
| | Iceross Clear | Silicone elastomer | 3.36 (0.10) |
| Silipos: New York. New York | SiloLiner | Silicone gel w/fabric backing | 5.21 (0.11) |
| TEC Interface Systems: Waite Palk. Minnesota | Pro 18 | Urethane | 6.29 (0.03) |

*Definition as a silicone gel or silicone elastomer was based on statements in the manufacturers' product literature.
†"Gel silicone" is a terms used by this manufacturer. Content and structure are not described to product literature.

Alternative Materials and Methods

Every interface between man and machine is fundamentally an interface between foreign materials and native cells. Managing this human interface then becomes an exercise in understanding how to best interface with cells. The language of cells is biological, molecular, and microscopic.

It is true, that many interfaces have been successful though they have been designed with a focus on bulk properties only, such as cloth interfaces on healthy tissues. But many times there is a disparity between cellular environment the assistive technology can provide and the needs of the cells. Such an example is the micro climate in the soft tissue interface between the residual limb of an amputee, and the artificial materials used to form the prosthesis.

However a focus on the cellular interface is preferable for developing a device for use on the outer surface of the body as well.

The Material Properties of Interest
1) Young's modulus/elasticity
2) Moisture Permeability
2) How are Materials Tested?

Major findings from: "Testing of elastomeric liners used in limb prosthetics: Classification of 15 products by mechanical performance" Joan E. Sanders, PhD; Brian S. Nicholson, BS; Santosh G. Zachariah, PhD; Damon V. Cassisi, BSME; Ari Karchin, MSE; John R. Fergason, CPO, Departments of Bioengineering and Rehabilitation Medicine, University of Washington, Seattle, Wash.

A number of different elastomeric liner products are available, and manufacturers and users claim they vary in Table taken from Sanders "Testing of elastomeric liners used in limb prosthetics: Classification of 15 products by mechanical performance"

The difference between silicone elastomers and silicone gels is their cross-linking and fluid retention. Silicone elastomers are extensively crosslinked and contain little free polydimethylsiloxane (PDMS) fluid. Silicone gels have lightly cross-linked polysiloxane networks, swollen with PDMS fluid. Since the PDMS fluid is not chemically bound to the network in silicone gels, fluid can bleed out of the gels.

Thus no conclusions can be drawn about durability. Durability was, however, a topic of previous investigations. Second, testing was conducted under interface loading conditions reflecting those measured at a number of interface locations during walking but not at the patellar-tendon. Thus stresses applied during testing here were lower than patellar-tendon stresses or those experienced during running. High activity, such as running, could induce sweating that could further alter mechanical response.

Several of the liner products had fabric backings on their external surfaces in contact with the socket. The results here showed that the backings' effects on liner tensile stiffness were minimal.

Major Findings from: "Moisture Permeability of the Total Bearing Socket with a Silicone Liner: is it Superior to the Patella-Tendon Bearing Sock":

Shows no large appreciable differences between liner materials.

But they note that silicone liner is not superior to the PTB socket with regard to moisture permeability, and that it is necessary to develop a new prosthetic socket that allows more heat release and the drainage of sweat. (Hachisuka, 2001)

The thermal conductivity of prosthetic sockets and liners (2007). Hachiuska, K., Matsushima, Y., Ohmine, S., Shinkoda, K., "Moisture permeability of the total surface bearing prosthetic socket with a silicon liner: Is it superior to the patella-tendon bearing prosthetic socket?" Arch. Physic. Med. Rehabil., 82 (2001) 1286-1289.

FIG. 2 illustrates the preparation process and structure of nanocomposite gels: a) clay particles are dispersed in monomer solution; b) initiator is added (which may preferentially adsorb on clay surface); c) polymerization of monomer occurs and polymer chains adsorb on the clay surface; d) final gel structure (as-prepared condition).

Note on Porosity:

Several references herein to "porosity," "porous," "pores," etc. A brief explanation and clarification is needed.

|  | Fabric cover | Thermal conductivity (W/m · °K) | Thickness (mm) | Product description |
|---|---|---|---|---|
| Liner |  |  |  |  |
| Pelite[1] | N | 0.085 | 4.2 | Closed cell foam |
| Syncor, Durasleeve[2] | Y | 0.085 | 3.5 | Closed cell foam |
| Bocklite[3] | N | 0.091 | 6.0 | Closed cell foam |
| OWW, Alpha Original[3] | Y | 0.114 | 3.0 | Mineral oil gel |
| OWW, Alpha Max[2] | Y | 0.128 | 6.0 | Mineral oil gel |
| OWW, P-pod[2] | Y | 0.143 | 3.0 | Mineral oil gel |
| OWW, Alpha Spirit[2] | Y | 0.155 | 6.0 | Mineral oil gel |
| ALPS, EZLiner HP Fabric[2] | Y | 0.164 | 6.0 | Silver in gel |
| Centri, Cushion Liner[1] | N | 0.164 | 3.0 | Thermoplastic elastomer |
| Euro International, Contex-Gel Streifeneder[1] | Y | 0.166 | 6.0 | Polymer gel |
| Freedom Innovations, Evolution SP[5] | N | 0.181 | 3.0 | Platinum cured silicone |
| ALPS, VIVA Sleeve[2] | Y | 0.182 | 6.0 | Gel |
| Medipro, RELAX[2] | Y | 0.182 | 6.0 | Silicone with Umbrellan ® |
| Silipos, Explorer Gel Liner[2] | Y | 0.184 | 6.0 | Mineral oil gel |
| ESP, Aegis Streamline[2] | Y | 0.187 | 6.0 | Pure silicone |
| ESP, Aegis Streamline[2] | N | 0.189 | 6.0 | Pure silicone |
| Medipro Sensitive[2] | Y | 0.194 | 6.0 | Silicone |
| ALPS, VIVA Sleeve HP Fabric[2] | Y | 0.202 | 6.0 | Gel |
| Ossur, IceRoss Dermo Seal-in[6] | Y | 0.205 | 6.0 | Dermogel ® |
| Euro International, Silicone First Class Liner[4] | Y | 0.212 | 6.0 | Silicone |
| ESP, Aegis Ultimate[2] | Y | 0.225 | 6.0 | Pure silicone |
| Ottobock, Silicone Liner[3] | Y | 0.228 | 3.0 | Silicone gel |
| Ossur, IceRoss Comfort Plus Sensil Gel[6] | Y | 0.266 | 6.0 | Soft Sensil ® silicone gel |
| Socket |  |  |  |  |
| Carbon fibre lay-up |  | 0.148 | 4.2 |  |
| Thermoplastic |  | 0.150 | 4.6 |  |

OWW, Ohio Willow Wood;
ESP, Engineered Silicone Products. Suppliers:
[1]Fillauer, Chattanooga, TN;
[2]Southern Prosthetic Supply, Paso Robles, CA;
[3]Otto Bock, Minneapolis, MN;
[4]Euro International, Tampa, FL;
[5]Freedom Innovations, Irvine, CA;
[6]Ossur, Aliso Viejo, CA.

New hydrogels have recently been developed having increased durability. Previously, swollen hydrogels where weak, crumbling and fracturing under pressure. New types of hydrogels known as dual network hydrogels have increases strength and bridge the gap between traditional rubbers and traditional hydrogels. According to the present disclosure, dual network hydrogels preferably may be used in composites to improve thermal conductivity as well as moisture permeability in various applications including prosthetic socket liners.

FIG. 1 shows the fracture energy of various materials vs their modulus: conventional hydrogels (open square); DN hydrogels (filled star); elastomers (half-filled square); ceramic glasses (filled circle); plastics (diamond); metals (filled triangle). It should be noted that the toughness values for the DN hydrogels have been corrected, because the original references used incorrect formulae for calculating the fracture energy from trouser tear test results.

Polymeric elastomer materials can generally be thought of as large sponges of entangled polymer chains soaked in a pool of liquid. In the case of silicone, silicone chains are entangled and swollen with silicone oil. This makes them impermeable to water. No water vapor of water liquid can pass through that material. In a molecular level there are free spaces between the chains and oil can flow and pass through. This flow can be measured and a "NET EFFECTIVE POROSITY" can be calculated. This does not mean that there are holes in the silicone, but rather that a pore equivalent behavior can be observed in certain conditions. Hydrogels can similarly be modeled as a swollen network of polymer chains. The chain network is swollen with water. A similar "NET EFFECTIVE POROSITY" can be calculated which described the viscous flow of water through the network, though no actual direct paths, or "holes", or "pores" exist. This fictional pore is what allows water to pass through the hydrogel, and is on the order of the diameter of a molecule of water or about 2 angstroms. This is in contrast to the "POROUS ELASTOMER" layers that have large holes on the order of microns or millimeters. This is also in contrast to expanded Teflon sheets such as Gortex which have pores that can be observed under magnification. Gortex Pores are true holes and allow vapor and gas through, but are not the correct diameter for passage of liquid water. Hydrogels do not allow gas to flow through them, only liquid water via viscous flow.

SUMMARY

One aspect of a preferred embodiment of the present disclosure comprises a moisture permeable composite material for a wide variety of applications including without limitation prosthetic liners, orthotic liners, clothing, space suits and environmental suits comprising: an inner layer comprising a hydrogel, a thin tough hydrogel membrane, or dual network hydrogel; and an outer layer comprising a porous elastomer or an open cell foam.

Another aspect of a preferred embodiment of the present disclosure comprises a moisture permeable composite material for a wide variety of applications including without limitation prosthetic liners, orthotic liners, clothing, space suits and environmental suits comprising: an inner layer, a middle layer and an outer layer;

In another aspect of a preferred moisture permeable composite material of the present disclosure, the inner layer comprises a material allowing for transmission of water in liquid and/or droplet form; the middle layer comprises a material to transfer water in liquid and/or droplet form away from the inner layer by viscous flow; and the outer layer comprises a porous material.

In yet another aspect of a preferred moisture permeable composite material of the present disclosure, the middle layer comprises a thin tough hydrogel membrane.

In another aspect of a preferred moisture permeable composite material of the present disclosure, the inner layer comprises a porous open cell foam.

In yet another aspect of a preferred moisture permeable composite material of the present disclosure, the inner layer comprises a porous elastomer.

In another aspect of a preferred moisture permeable composite material of the present disclosure, the outer layer comprises porous elastomer.

A further aspect of a preferred embodiment of the present disclosure comprises a moisture permeable composite material for a wide variety of applications including without limitation prosthetic liners, orthotic liners, clothing, space suits and environmental suits comprising: an inner layer comprising a thin tough hydrogel membrane, a hydrogel or a dual network hydrogel; and one or more other layers comprising an open cell foam and/or a porous elastomer material.

Another aspect of a preferred embodiment of the present disclosure comprises a system for removing moisture from a residual limb inserted in a prosthesis comprising: a nonporous prosthesis socket; a liner disposed in the socket wherein the liner comprises a inner layer comprising a thin tough hydrogel membrane, a hydrogel or dual network hydrogel; and an outer layer comprising a porous elastomer material or an open cell foam; a nonporous seal that prevents air leakage from the space between the socket and the liner to the outside environment; and a vacuum source to reduce the pressure in the space between the socket and liner.

An additional aspect of a preferred embodiment of the present disclosure comprises a system for removing moisture from a residual limb inserted in a prosthesis comprising: a nonporous prosthesis socket; a liner disposed in the socket wherein the liner comprises a middle layer comprising a thin tough hydrogel membrane, a hydrogel or a dual network hydrogel; an inner layer comprising a porous elastomer or an open cell foam material; and an outer layer comprising a porous cushioning material; a nonporous seal that prevents air leakage from the space between the socket and the liner to the outside environment; and a vacuum source to reduce the pressure in the space between the socket and liner.

In another aspect of a preferred system for removing moisture from a residual limb inserted in a prosthesis of the present disclosure, the inner layer is disposed throughout the entire liner.

In yet another aspect of a preferred system for removing moisture from a residual limb inserted in a prosthesis of the present disclosure, the middle layer is disposed throughout the entire liner.

In another aspect of a preferred system for removing moisture from a residual limb inserted in a prosthesis of the present disclosure, the inner layer is disposed throughout only a portion and not the entirety of the liner.

In a further aspect of a preferred system for removing moisture from a residual limb inserted in a prosthesis of the present disclosure, the middle layer is disposed throughout only a portion and not the entirety of the liner.

In another aspect of a preferred system for removing moisture from a residual limb inserted in a prosthesis of the present disclosure, the inner layer is convoluted for increased surface area.

In another aspect of a preferred system for removing moisture from a residual limb inserted in a prosthesis of the present disclosure, the middle layer is convoluted for increased surface area.

Another aspect of a preferred embodiment of the present disclosure comprises a system for removing moisture from a residual limb inserted in a prosthesis comprising: a nonporous prosthesis socket; a liner disposed in the socket wherein the liner comprises a first layer comprising a hydrogel or thin tough hydrogel membrane or dual network hydrogel disposed in a second layer comprising a porous silicone cushioning material; a nonporous seal that prevents air leakage from the space between the socket and the liner to the outside environment; and a vacuum source to reduce the pressure in the space between the socket and liner.

In another aspect of a preferred system for removing moisture from a residual limb inserted in a prosthesis of the present disclosure, the first layer is disposed throughout the entire liner.

In yet another aspect of a preferred system for removing moisture from a residual limb inserted in a prosthesis of the present disclosure, the first layer is disposed throughout only a portion and not the entirety of the liner.

In another aspect of a preferred system for removing moisture from a residual limb inserted in a prosthesis of the present disclosure, the first layer comprises a convoluted membrane for increased surface area.

In an additional aspect of a preferred system for removing moisture from a residual limb inserted in a prosthesis of the present disclosure, the outer layer comprises a fiber material, a nanomaterial or other reinforcing material.

In another aspect of a preferred system for removing moisture from a residual limb inserted in a prosthesis of the present disclosure, one or more of the inner, middle and outer layers comprises a fiber material, a nanomaterial or other reinforcing material.

In yet another aspect of a preferred system for removing moisture from a residual limb inserted in a prosthesis of the present disclosure, one or more of the inner and outer layers comprises a fiber material, a nanomaterial or other reinforcing material.

In another aspect of a preferred system for removing moisture from a residual limb inserted in a prosthesis of the present disclosure, one or more of the inner, middle and outer layers comprises a fiber material, a nanomaterial or other reinforcing material.

In a further aspect of a preferred system for removing moisture from a residual limb inserted in a prosthesis of the present disclosure, one or more of the first and second layers comprises a fiber material, a nanomaterial or other reinforcing material.

In another aspect of a preferred system for removing moisture from a residual limb inserted in a prosthesis of the present disclosure, the outer layer defines a plurality of pores of one or more shapes selected from the group consisting of a cylinder, a cone, a bell, a trumpet and a geometric shape.

An additional aspect of a preferred embodiment of the present disclosure comprises a method for forming a thin tough hydrogel, comprising: curing with UV light a first monomer solution to form a membrane; soaking the membrane in a second monomer solution in a UV transparent tray having a drain; draining excess second monomer solution from the UV transparent tray; and curing with UV light the membrane soaked with the second monomer solution in the UV transparent tray with or without a UV transparent cover.

BRIEF DESCRIPTION OF THE DRAWINGS

The present disclosure is illustrated by way of example and not limitation in the figures of the accompanying drawings, in which:

FIG. 1 shows fracture energy of various materials vs their modulus: conventional hydrogels (open square); DN hydrogels (filled star); elastomers (half-filled square); ceramic glasses (filled circle); plastics (diamond); metals (filled triangle) (it should be noted that the toughness values for the DN hydrogels have been corrected, because the original references used incorrect formulae for calculating the fracture energy from trouser tear test results);

FIG. 2 illustrates the preparation process and structure of nanocomposite gels: a) clay particles are dispersed in monomer solution; b) initiator is added (which may preferentially adsorb on clay surface); c) polymerization of monomer occurs and polymer chains adsorb on the clay surface; d) final gel structure (as-prepared condition);

FIG. 6 shows a system for removing moisture from a residual limb inserted in a prosthesis according to the present disclosure;

FIG. 7 shows a system for removing moisture from a residual limb inserted in a prosthesis according to the present disclosure;

FIG. 8 shows a preferred moisture permeable hydrogel composite material according to the present disclosure comprising just two layers, i.e., an inner layer (top layer shown) and an outer layer (bottom layer shown);

FIG. 9 shows another preferred moisture permeable hydrogel composite material according to the present disclosure comprising just two layers, i.e., an inner layer (top layer shown) and an outer layer (bottom layer shown);

FIG. 10 shows yet another preferred moisture permeable hydrogel composite material according to the present disclosure comprising just two layers, i.e., an inner layer (top layer shown) and an outer layer (bottom layer shown);

FIGS. 21A-21B schematically depict another preferred method of manufacturing a hydrogel membrane of the present disclosure;

FIGS. 22A-22B show a preferred embodiment of a thin tough hydrogel membrane according to the present disclosure;

DETAILED DESCRIPTION

In the following detailed description, reference is made to the accompanying examples and figures that form a part hereof, and in which is shown by way of illustration specific embodiments in which the inventive subject matter may be practiced. These embodiments are described in sufficient detail to enable those skilled in the art to practice them, and it is to be understood that other embodiments may be utilized and that structural, logical, and electrical changes may be made without departing from the scope of the inventive subject matter. Such embodiments of the inventive subject matter may be referred to, individually and/or collectively, herein by the term "disclosure" merely for convenience and without intending to voluntarily limit the scope of this application to any single disclosure or inventive concept if more than one is in fact disclosed.

The following description is, therefore, not to be taken in a limited sense, and the scope of this disclosure is defined by the appended claims.

Figure 3:
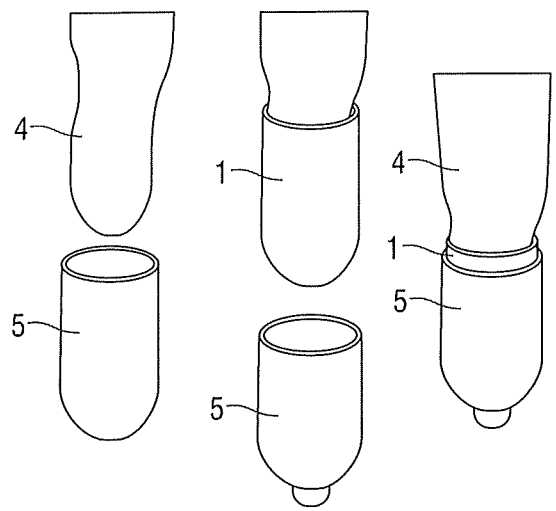
FIG. 3 shows a prosthetic interface worn on a residual limb between the skin and a socket shell.

A preferred aspect of the present disclosure is a moisture permeable prosthetic liner system employing a thin water permeable hydrogel membrane. Moisture permeable hydrogel membranes have never been used in this way or for this purpose. It is an FDA class 1 device. A prosthetic interface 1 is worn on the residual limb 4 between the skin and the hard socket shell 5, it cushions and protects the limb (FIG. 3). Currently prosthetic liners are typically made of moisture impermeable materials such as silicone.

Figure 4:
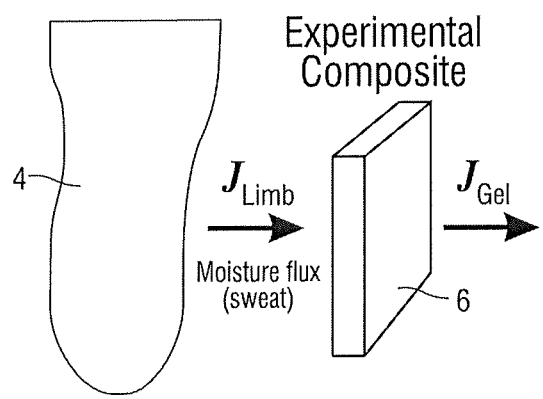
FIG. 4 is an illustration showing that flux through the membrane (J-Gel) should be comparable to flux of sweat (J-Limb) through skin.

How it Works:

FIG. 3 shows a prosthetic interface is worn on the residual limb between the skin 4 and the socket shell 5. Using a vacuum system the hydrogel membrane will be exposed to a negative pressure on one side, this negative pressure creates a gradient which is used to draw moisture from the opposite side of the membrane, i.e., the side adjacent the residual limb (FIG. 4). The moisture is drawn through in a manner described as viscous flow. Viscous flow occurs when the water in liquid form permeates through the hydrogel polymer in a fashion similar to the permeation of water through porous sand. As shown in FIG. 4, preferably flux through the membrane (J-Gel) should be comparable to flux of sweat (J-Limb) through skin.

The prerequisite for the use of the Darcy flow equation in a hydrogel is to determine whether or not viscous fluid flow or diffusive fluid flow is dominant within the thickness of the hydrogel. This is done by considering the state of the hydrogel required for viscous flow.

Permeability:

Governing equation for viscous flow of fluid through hydrogel:

$$K = \frac{V * L * \eta}{t * A * \Delta P} \quad *[\text{white}, 1960]$$

$K$ = permeability coefficient of membrane (cm$^2$)
$V$ = volume of liquid (mL)
$\eta$ = viscosity of fluid permeating through membrane (Poises) or (P)
$t$ = time (seconds) or (s)
$A$ = area (cm$^2$)
$\Delta P$ = pressure differential across membrane (dynes/cm$^2$)

Conversion Factors:

Pa = Pascal $1 \text{ Poise} = .1 \frac{\text{kg}}{\text{m} * \text{s}} = 1 \frac{\text{g}}{\text{cm} * \text{s}} = .1 \text{ Pa} * \text{s} = 1 \text{ P}$ $1 \text{ dyne} = 10^{-5} \frac{\text{kg} * \text{m}}{s^2} = 1 \frac{\text{g} * \text{cm}}{s^2} = 10^{-5} \text{ N}$ $1 \text{ mm } HG \approx 1 \text{ Torr} = 133.32244 \text{ Pa}$ $1 \text{ P} = 1 \text{ Poise} = .1 \text{ Pa} * \text{s}$ $1 \text{ cP} = 1 \text{ mPa} * \text{s} = .001 \text{ Pa} * \text{s} = 1 \frac{\text{N} * \text{s}}{\text{m}^2}$ $1 \text{ day} = 84,600 \text{ s}$ $1 \text{ m}^2 = 10,000 \text{ cm}^2$ $1 \text{ Liter } H_2O = 1 \text{ kg } H_2O$ Known Constants from Literature Temperature of residual limb in socket ≈30°-33° Celsius *[Perry, Ledoux, Klute, 2005]

Viscosity H$_2$O @ 30° C.=797.3 µPa*s=0.007973P [Kesitn, Sokolv, Wakeham, 1978]

Viscosity sweat @ 30° C.=0.8 cP *[Emrich Stoll, Friolet, Columbo, Richter, Rossi, 1968]

Sweat rate in hot weather, or $\text{high exertion} = 2.4 \frac{\text{kg}}{\text{m}^2 * \text{day}} = .1 \frac{\text{L}}{\text{m}^2 * \text{hour}} = 2.77 * 10^{-6} \frac{\text{mL}}{\text{cm}^2 * \text{s}}$

*[Fergeson-Pell, Hirose, Nicholson, Call, 2009]

H$_2$O % of supertough D.N. Hydrogels ≈90% *[Haque, Kurokowa, Gong, 2012]

Permeability coefficient GMA @89.2% H$_2$O=19.96*10$^{-16}$±0.61*[Refojo, 1965]

Vacuum Pressure from prosthetic pump: 8-20 inches Hg=270,800-670,00 dynes

Calculation of Surface Area of Residual Limb in Socket:
Surface are outer curved surface only=$2\pi r^2$
Surface Area excluding both bases=$pi(A+B)sqrt(B-A)^2+H^2]$ Using a medium sized Ohio WillowWood Alpha Classic AK Liner as an approximation for a residual limb size, the dimensions are:
r=3.131 cm
a=3.131 cm
b=5.411 cm
h=26.0 cm
*[willowood.com]

Calculations done with these equations and information can easily show, that for an optimistic permeability of a 90% water hydrogel, and for vacuum pressures of a reasonably accessible level through currently available vacuum pumps in the prosthetic fields, the thickness of the hydrogel membrane should be 1 mm or less to be effective as a moisture permeable membrane. Therefore, when referring to the thin tough hydrogel membrane herein, the thickness of the membrane is calculated using these equations depending upon the available vacuum source, total area of the membrane, and water content of gel. The thin tough hydrogel membranes for the application in moisture permeable prosthetic limb liners preferably is less than 1 mm in thickness.

Figure 5:
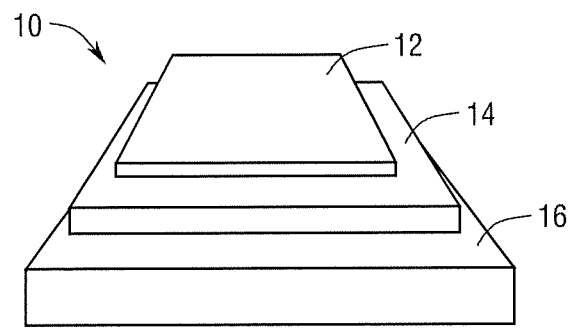
FIG. 5 shows a preferred moisture permeable hydrogel composite material according to the present disclosure comprising an inner layer (top layer shown) comprising a hydrogel or thin tough hydrogel or dual network hydrogel; a middle layer comprising an open cell foam material; and an outer layer (bottom layer shown) comprising a porous cushioning material.

Advantages to Subatmospheric Pressure
http://www.oandp.com/articles/2012-07_01.asp Description of the Layers of the Composite Liner In a preferred embodiment, composite material 10 according to the present disclosure for use as a prosthetic socket liner 1, among other various uses, preferably comprises three layers, see FIG. 5. The top layer 12 is a water permeable membrane. The second layer 14 is an interface, or bonding layer which may have some wicking properties. The thickest layer 16 is primarily a cushioning layer with moisture transfer pores or perforations.

Current prosthetic liners are compliant enough to cushion the user's residual limb to a satisfactory degree. Current liners do not allow for the escape of moisture. A preferred composite liner 1 according to the present disclosure will retain the mechanical properties of the existing liners but will also allow moisture to escape.

To achieve these aims the preferred composite liner 1 according to the present disclosure will be a composite material. The liner 1 will be made of different layers (preferably two or three layers) bonded together, each of which will play a role in helping the liner to function properly. Among the layers will be the key enabling technology, the hydrogel membrane shown in FIG. 3 as the top layer 12, preferably a tough dual network hydrogel layer and the thinnest layer. Its thickness will be comparable to other comparable membranes such as Gortex. However, unlike Gortex, which only allows for the flow of water in a vaporized state, the hydrogel layer 12 will allow for the transmission of water in a liquid droplet form by viscous flow. The second layer 14 preferably comprises a porous open cell foam layer. This middle layer 14 will be used as a wicking layer to help draw the water away from the hydrogel membrane layer 12 and direct it to drainage holes. The outer layer 16 is a porous silicone layer. The silicone will be used to provide a compliant layer to cushion the limb. It will be full of pores or holes through which the water may pass and drain away from the residual limb 4.

Simply perforating traditional liners is not feasible as doing so reduces or negates necessary linkage. Linkage is the property of a prosthetic liner wherein it binds the residual limb 4 to the prosthetic limb. Modern prosthetic sockets rely on suction to provide linkage to the limb 4. Putting perforations in the socket liner would allow for the rapid flow of air and loss of suction negating linkage. The preferred composite liner 1 according to the present disclosure with the inner hydrogel membrane 12 provides a mechanism whereby the suction is maintained while allowing only the moisture to permeate through and not vapor or gas flow. This approach has not been done before.

FIGS. 6 and 7 show a preferred system 20 for removing moisture from a residual limb inserted in a prosthesis according to the present disclosure comprising: a nonporous prosthesis socket 26; a liner 1 disposed in the socket 26 wherein the liner 1 comprises an inner layer 32 comprising a hydrogel or thin film hydrogel or dual network hydrogel; a middle layer 30 comprising an open cell foam wicking material; and an outer layer 28 or 29 comprising a porous silicone cushioning material; a nonporous seal 24 that prevents air leakage from the space between the socket 26 and the liner 1 to the outside environment; and a vacuum source 22 to reduce the pressure in the space between the socket 26 and liner 1.

In another preferred embodiment shown in FIG. 8, the present disclosure comprises a system for removing moisture from a residual limb inserted in a prosthesis comprising: a nonporous prosthesis socket 26; a liner 1 disposed in the socket wherein the liner comprises a first layer 32 comprising a hydrogel or thin film hydrogel or dual network hydrogel disposed in a second layer 33 comprising a porous silicone cushioning material; a nonporous seal (see 24 in FIG. 7) that prevents air leakage from the space between the socket 26 and the liner 1 to the outside environment; and a vacuum source 22 to reduce the pressure in the space between the socket 26 and liner 1. The first layer 32 may be disposed throughout the entire liner 1 or throughout only a portion thereof and not the entirety of the liner 1 as shown in FIGS. 9 and 10. The first layer 37 may preferably comprise a folded layer or folded membrane for increased surface area as shown in FIG. 10.

In all embodiments of the composite liner 1 according to the present disclosure, the hydrogel layer may be disposed throughout the entire liner 1 or throughout only a portion and not the entirety of the liner 1. Also, the hydrogel layer may preferably comprise a folded layer or folded membrane for increased surface area.

Preferably, dual network hydrogels will be used according to the present disclosure because they have excellent elongation properties, as well as excellent tensile strength. Also nanocomposite hydrogels may also be preferred due to their improved properties as well, but also because of their ease of preparation. Homogeneously cross linked hydrogels may also be promising but may also require sophisticated formation techniques. Other hydrogels can be difficult to produce and may not have as favorable a range of properties.

Figure 11:
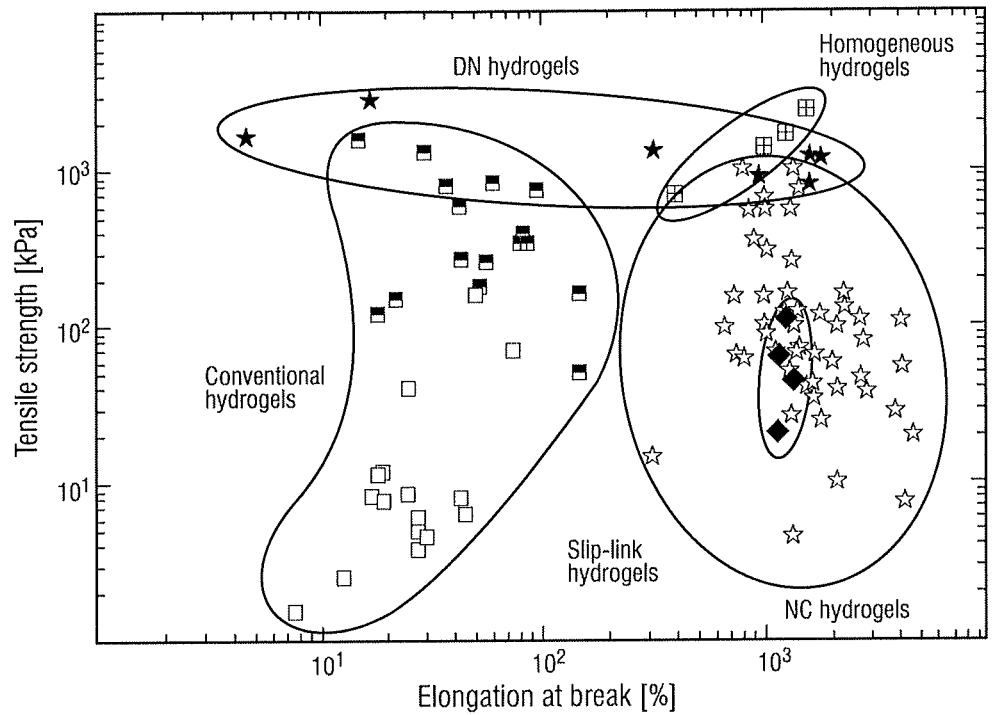
FIG. 11 shows tensile strength of various hydrogels and gels vs their corresponding elongation at break: conventional single network hydrogels (including from hydrophilic homopolymers—open square; and copolymers using a hydrophobic co-monomer-half-filled square); DN hydrogels (filled star); NC hydrogels (open star); homogeneous hydrogels (crossed square); slip-link hydrogels (filled diamonds)

FIG. 11 shows tensile strength of various hydrogels and gels vs their corresponding elongation at break: conventional single network hydrogels (including from hydrophilic homopolymers—open square; and copolymers using a hydrophobic co-monomer-half-filled square); DN hydrogels (filled star); NC hydrogels (open star); homogeneous hydrogels (crossed square); slip-link hydrogels (filled diamonds).

Figure 12:
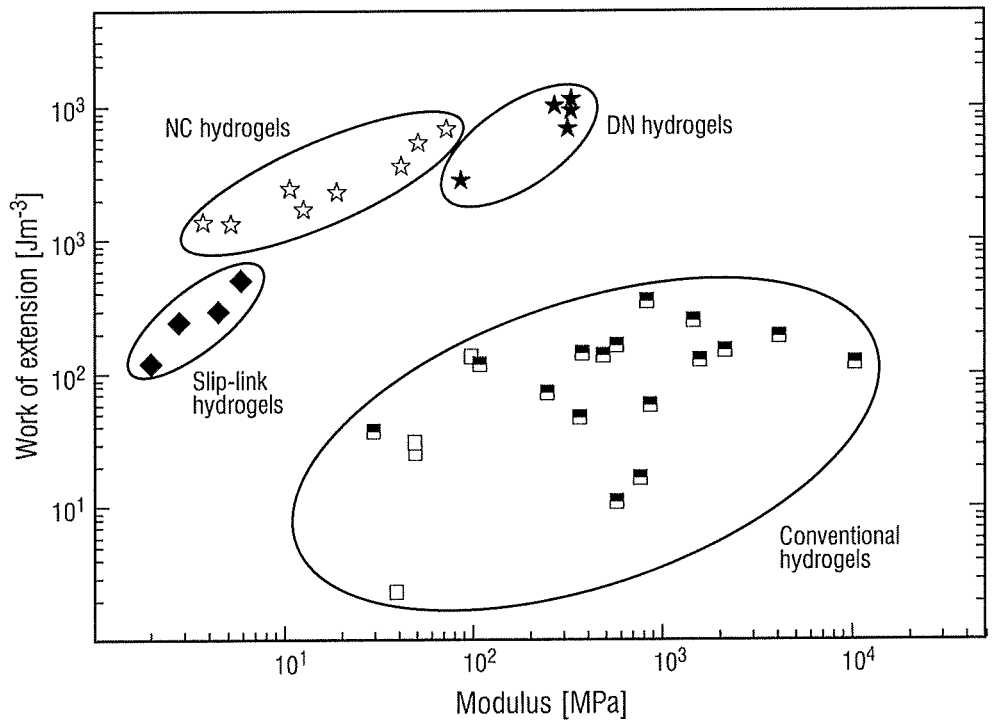
FIG. 12 illustrates work of extension of various hydrogels and gels and their corresponding Young's modulus; conventional single network hydrogels (including from hydrophilic homopolymers—open square; and copolymers using a hydrophobic co-monomer-half-filled square); DN hydrogels (filled star); NC hydrogels (open star); homogeneous hydrogels (crossed square); slip-link hydrogels (filled diamonds)

FIG. 12 shows work of extension of various hydrogels and gels and their corresponding Young's modulus; conventional single network hydrogels (including from hydrophilic homopolymers—open square; and copolymers using a hydrophobic co-monomer-half-filled square); DN hydrogels (filled star); NC hydrogels (open star); homogeneous hydrogels (crossed square); slip-link hydrogels (filled diamonds).

A preferred dual network hydrogel recipe may be used, for example, from the following article: Biomaterials 26 (2005) 4468-4475 Biomechanical properties of high-toughness double network hydrogels: "PAMPS-PAAm"=poly(2-acrylamide-2-methyl-propane sulfonic acid)-polyacrylamide.

Recipe: For the first network:
1) 2-Acrylamido-2-methylpropanesulfonic acid (AMPS) 1 kg 39.40$ http://www.sigmaaldrich.com/catalog/product/aldrich/282731?lang=en®ion=US
2) also needed is a cross linker N,N'-Methylenebis(acrylamide) 100G 34.10$ http://www.sigmaaldrich.com/catalog/product/sial/146072?lang=en®ion=US
3) Also need photo initiator 2-Oxoglutaric acid 100G 84.00$ http://www.sigmaaldrich.com/catalog/product/fluka/75890?lang=en®ion=US
3) Acrylamide 1 kg 110.50$ http://www.sigmaaldrich.com/catalog/product/fluka/01700?lang=en&region=US The Harmony system by Ottobock is capable of puling between 15-25 inches Hg. http://professionals.ottobockus.com/cps/rde/xbcr/ob_us_en/04020441.1D_HarmonyP 2_HD_IF U.pdf Limb logic vacuum pump for use in accordance with the present disclosure can do about 22 mmhg.

Compression:

In addition to the permeability aspects of the prosthetic liner 1, another critical aspect is the mechanical loading characteristics.

Figure 13:
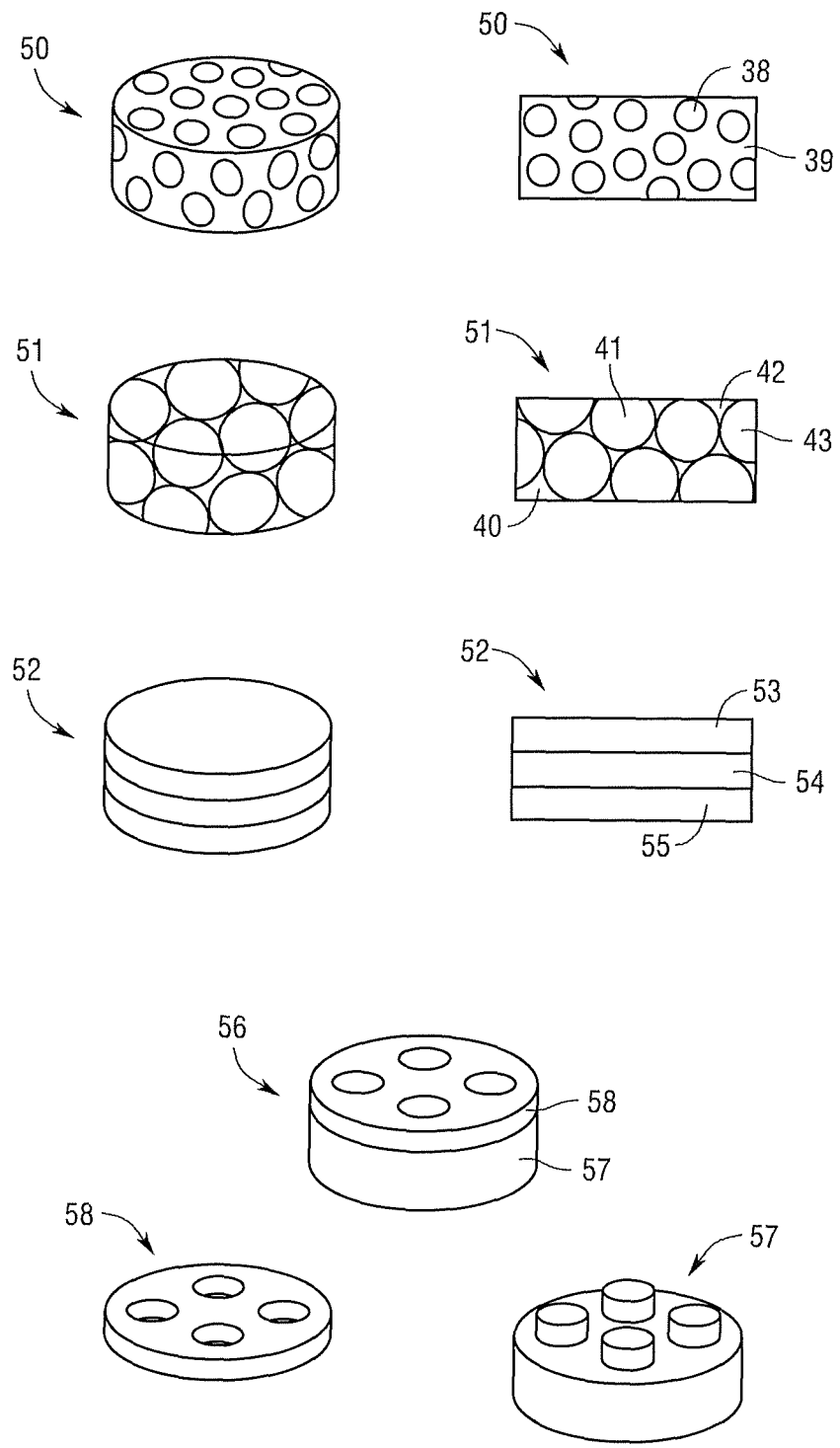
FIG. 13 shows various components of a moisture permeable prosthetic liner according to the present disclosure comprising one or more complex composite materials.

As shown in FIG. 13, the moisture permeable prosthetic liner according to the present disclosure preferably may take the form of a complex composite of multiple materials. Preferably, hydrogel composite 50 or 51 of FIG. 13 may take one of two forms. In the upper drawing labeled 50, the hydrogel composite takes the form of a homogeneously distributed dispersion of small silicone spheres 38 within the hydrogel matrix 39. Spheres 38 while shown to be made of silicone are not limited to silicone. They can be made of various other compatible polymers that will augment either the thermal transmission, mechanical strength, mechanical compliance or other material properties such as drug delivery or antibiotic delivery but not limited to drug or antibiotic delivery. The spheres 38 may even be made of differing types of hydrogel with material properties differing from that of the base matrix 40. The moisture from the interior of the liner will be able to permeate through the hydrogel matrix around the small spheres 38. The spheres 38 may be either on the macroscale or microscale. Microspheres are not easily identifiable to the naked eye, and are on the order or $1\times10^{-6}$ meters in diameter. Macrospheres would be larger than that and would be easily identifiable by the naked eye. The term "spheres" here denotes the general approximation of the particles as a spherical shape for the purpose of approximate computational modeling and may not actually reflect the true geometry of the particles 38. The particles 38 here referred to as microspheres may be amorphous in shape, oval, oblong or irregular, including cubic, or prismatic.

The interconnected granular design hydrogel composite 51 in general refers to the feature of the granular composite such that the particles within the composite 41, 43, are of such high concentration/density relative to the base matrix 42, 40, that the particles make physical contact with one another and are not isolated and separated by the base matrix as in the discreet granular composite 50. The drawing labeled granular interconnected features two separate designs separated by a dotted line. On the right side of the dotted line interconnected granular composite features an interconnected network of hydrogel particles 43 within a silicone base matrix 42. In this embodiment the water would be able to permeate through the particles of the hydrogel particles. For this to be possible the hydrogel particles are covalently bonded to one another forming one large interconnected network with no silicone separating them. The left side of the drawing features an interconnected network of silicone particles 41 embedded in a hydrogel base matrix 40, The water would be able to permeate through the base matrix as it would form an interpenetrating network of hydrogel filling the gaps between the particles.

These interconnected or discreet granular composites may be formed using well known bioengineering methods such as porogen leaching, emulsification, or 3d printing.

The section of FIG. 13 labeled 52, features a laminar composite. In this embodiment the composite the hydrogel has been layered in flat sheets one on top of another. As shown the layers 53, 54 and 55 may vary in material properties such as mechanical modulus, but the layers may also vary in other material properties such as moisture permeability, chemical formulation, thermal transitivity or others. The various layers of the laminar composite may be formed by covalently, ionically, or electrostatically joining separate individually formed thin layers or by consecutive forming of one layer one on top of the other in a sequential "one pot" method.

Interlocked composite 56 of FIG. 13 features specifically customized separate parts 58, 57 of materials that are in such a geometry so as to be interlocking and fit into one another with a very tight tolerance, such as pieces snap fit together such as Lego blocks.

Figure 14:
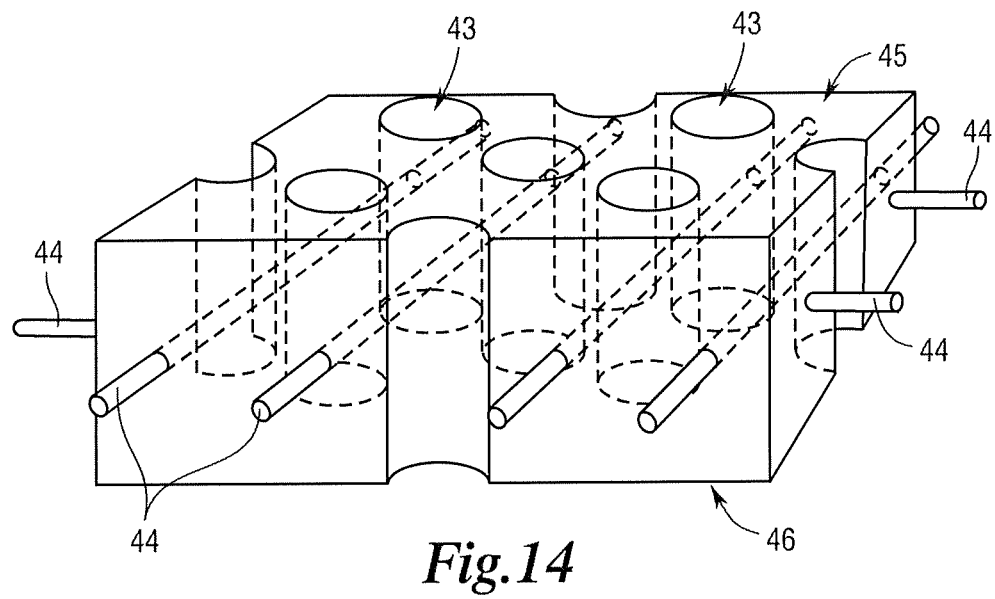
FIG. 14 depicts a preferred embodiment of a laminar composite layer of a perforated elastomer and hydrogel according to the present disclosure.

FIG. 14 depicts a preferred embodiment of a laminar composite layer 45 of perforated elastomer and hydrogel. The layer 45 is the perforated elastomer layer for a liner according to the present disclosure. Elastomer layer 45 comprises straight tubular pores 43 through which the moisture may pass down through the perforated elastomer layer 45 down to the hydrogel layer. Notable about this layer is the inclusion of a reinforced fiber network 44. The reinforced fiber network 44 is embedded into the perforated elastomer 45 to reinforce its tensile properties. The lateral tensile properties relative to the plane of the layer 45 are compromised by the presence of the pores for water transmission. To recapture the lateral strength and limit the total lateral stretch, the embedded fiber network 44 is included. Computer modeling would be required to fully specify the form of the fiber network required to recapture material strength depending upon the geometry of the pores required. As discussed elsewhere on the topic of pore geometry, the shape of the pores will vary depending upon need and application with a few examples given elsewhere within this disclosure. Also in the diagram the hydrophilic and hydrophobic surface treatment of the layer is depicted. As can be seen the top of the layer is hydrophobic, 45, and the bottom is hydrophilic, 46, the goal of this treatment would be to aid in driving water droplets downward through the pores to the bottom of the layer that would make contact with the hydrogel layer and from there would permeate through. One preferred material to use to form the fiber network 44 would be nylon though other materials are also useful for this purpose.

Figure 15:
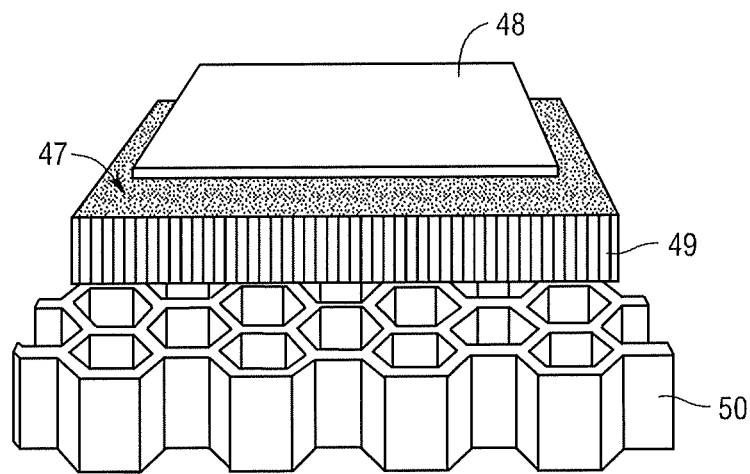
FIG. 15 shows is a preferred embodiment of a liner of the present disclosure comprising a thin tough hydrogel membrane, a wicking layer and a perforated elastomer hexagonal honeycomb cushioning layer.

Shown in FIG. 15 is another preferred embodiment of a liner 10 of the present disclosure comprising a wicking layer 49. Defined here, wicking refers to a gradient driven evaporative method of driving moisture away from the hydrogel layer 48. This would be similar to traditional wicking technology found in sportswear. Preferably, the laminar composite bonding 47 of the wicking material directly to the thin tough hydrogel membrane 48. Such construction results in a greater rate of water evacuation than traditional stand-alone hydrogels. This wicking layer 49 is referred to also as the evaporation layer because the greater surface evaporation rate of the wicking layer 49 to the air would pull the moisture through the hydrogel membrane 48 more quickly. An ideal method for bonding the two layers together would be plasma vapor deposition of the polymer monomers onto the surface of the wicking layer 49 followed by the addition of the hydrogel layer 48. As shown in FIG. 15, wicking layer 49 would require a high exposed surface area to be able to remove the moisture so a perforated elastomer hexagonal honeycomb layer 50 is shown which would provide cushioning as well as venting for the vapors.

Figure 16A:
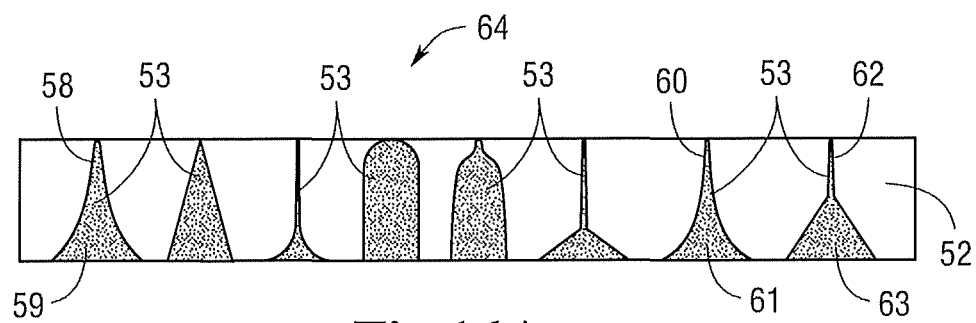
FIG. 16A shows various preferred pore types and/or shapes for various layers of moisture permeable composite materials of the present disclosure.

FIG. 16 shows various preferred configurations for the moisture permeable composite layer 64 of a liner 10 of the present disclosure. Preferably, pores 53 of various profiles are defined by composite transmission layer 64. FIG. 16A illustrates eight preferred pore types are shown, three of the pores are labeled 59, 61 and 63. 59, 61 and 63 are used to denote the surface of the plane of the layer which faces the thin tough hydrogel membrane. Preferably, the sides of the pores facing the thin tough hydrogel membrane in these embodiments terminate in a larger diameter opening. The reason for this is twofold. A large surface area is required for the efficient transmission of water through the hydrogel membrane. The presence of a large diameter pore opening would be uncomfortable for the user. The side of the transmission layer that makes contact with the skin, 58, 60 and 62 ought to have as small a pore opening diameter as possible. The transition of pore diameter from the very small on the side making contact with the user to the very wide on the side making contact with the hydrogel layer may be varied in a number of ways. The variance of the diameter along the length of the pore has a number of effects upon the properties of the transmission layer and give it various non constitutive properties. The mechanical characteristics of the transmission layer are affected differently according to the shape of the pore used. The shaded region in the 2D profile of the drawings of the pore represents the area of the cross section of the pore and is related to the volume of actual 3Dimensional pore. Thus the pores with larger shaded regions represent pores with lumens or greater volume. Pores with greater lumen remove a greater amount of structural material from the transmission layer 64 effectively lowering its mechanical modulus. The volume of the lumen of the pore also forms a small reservoir to contain a droplet of moisture and keep it away from the skin, and hold the droplet against the surface of the hydrogel membrane until it can permeate through. The shape of the pore also determines the extent of the capillary action that will take place. Capillary action would be helpful for removing moisture from the surface of the skin and transporting it to the hydrogel membrane for permeation. A tradeoff of these three properties needs to be done for the application at hand, the expected rate of moisture accumulation and permeation.

Figure 16B:
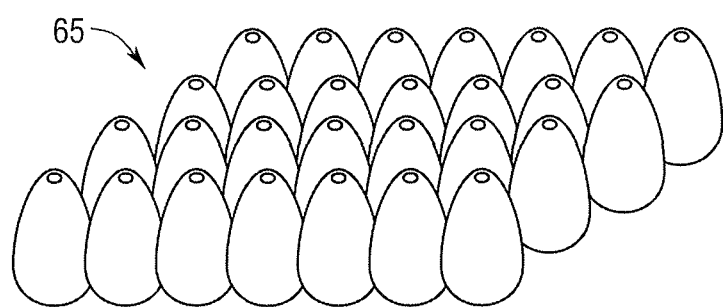
FIG. 16B is a depiction of the all the cumulative lumen volumes for a pore array within a flat piece of a moisture permeable composite material of the present disclosure.

FIG. 16B is a depiction of the all the cumulative lumen volumes 65 for a pore array within a flat piece of material. They represent the pieces of material 65 that would be removed to form the pores.

Figure 16C:
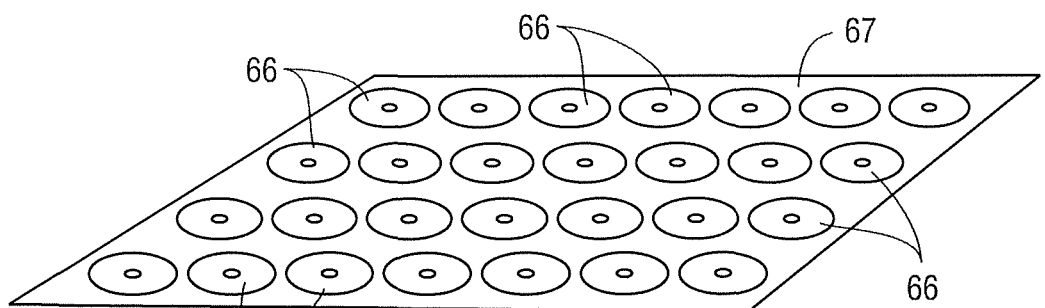
FIG. 16C shows the area available for moisture permeation within a moisture permeable composite material of the present disclosure.
Figure 17A:
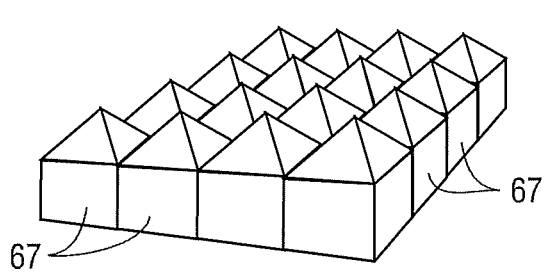
FIG. 17A shows an extreme case of the pore geometry such that the edges of the pores in a layer of a moisture permeable composite material of the present disclosure touch each other leaving minimal room for adherence and maximum room for moisture transmission.
Figure 17B:
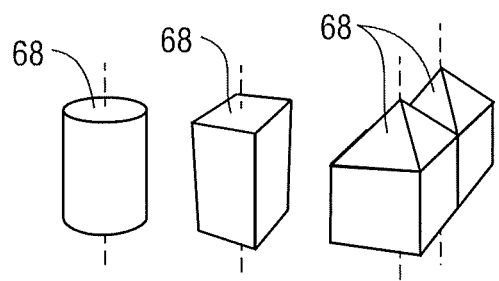
FIG. 17B illustrates a possible modeling of pore geometry using a 3D computer aided design modeling program.
Figure 17C:
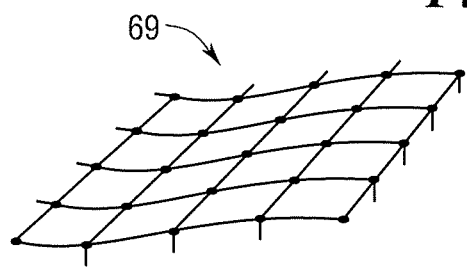
FIG. 17C illustrates a preferred coordinate system which would be needed to model the pores in a layer of a moisture permeable composite material of the present disclosure.
Figure 17D:
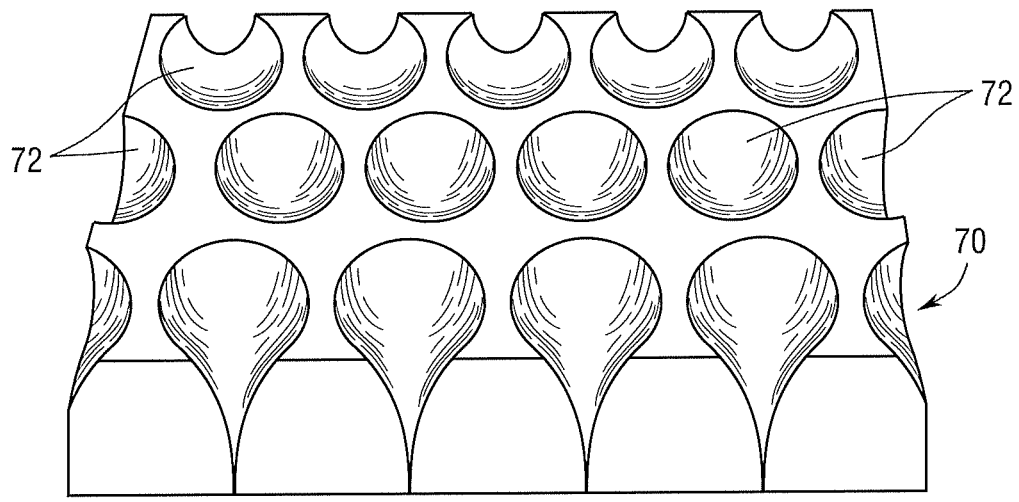
FIG. 17D shows a preferred transmission layer in a layer of a moisture permeable composite material of the present disclosure.
Figure 17E:
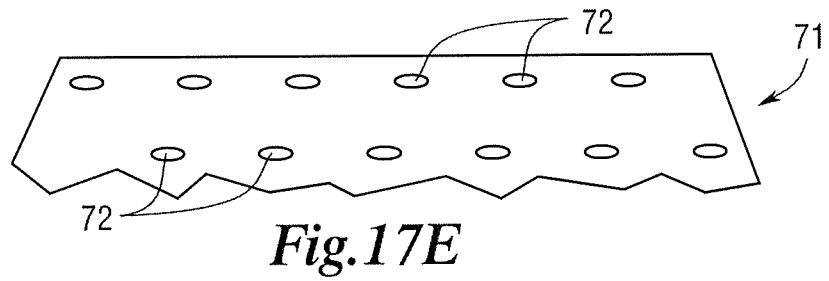
FIG. 17E is a mirrored view of the underside of the transmission layer of FIG. 17D showing the small size of the pores that would be faced outward to the surface of the user.

FIG. 16C shows the area available for moisture permeation. As the wide opening of the pore is against the hydrogel membrane, the area available for permeation is shown as enclosed by the circles 66. The enclosed circles 66 represent the area of the opening of the pores against the hydrogel membrane. The areas 67 in the square not in the circles is the area which adheres the transmission layer of the composite to the hydrogel layer. The area adhered to the hydrogel can be adhered by a variety of mechanisms including covalent bonding, glue, electrostatic adherence and others. As the area enclosed by the circles increases, the area available decreases this simultaneously weakens the adherence, and improves moisture permeability.

FIG. 17 illustrates further preferred pores. FIG. 17A, shows an extreme case of the pore geometry such that the edges of the pores 67 touch each other leaving minimal room for adherence and maximum room for moisture transmission. FIG. 17B illustrates a possible modeling of pore 68 geometry using a 3D computer aided design modeling program. FIG. 17 C illustrates a preferred coordinate system 69 which would be needed to model the pores. FIG. 17D shows a preferred transmission layer 70 with the side that would bond to the hydrogel layer facing upwards wherein each pore 72 has a conical profile with the large area to interface the transmission layer to the hydrogel layer. FIG. 17D also clearly shows the depth and shape of the pores 72 in a 3-dimensional depiction of a rectangular section of the layer. FIG. 17E is a mirrored view of the underside of the transmission layer 70 showing the small size of the pores 72 that would be faced outward to the surface of the user. Preferably, holes 72 are very small and designed so as not to be a nuisance to the user.

Figure 18:
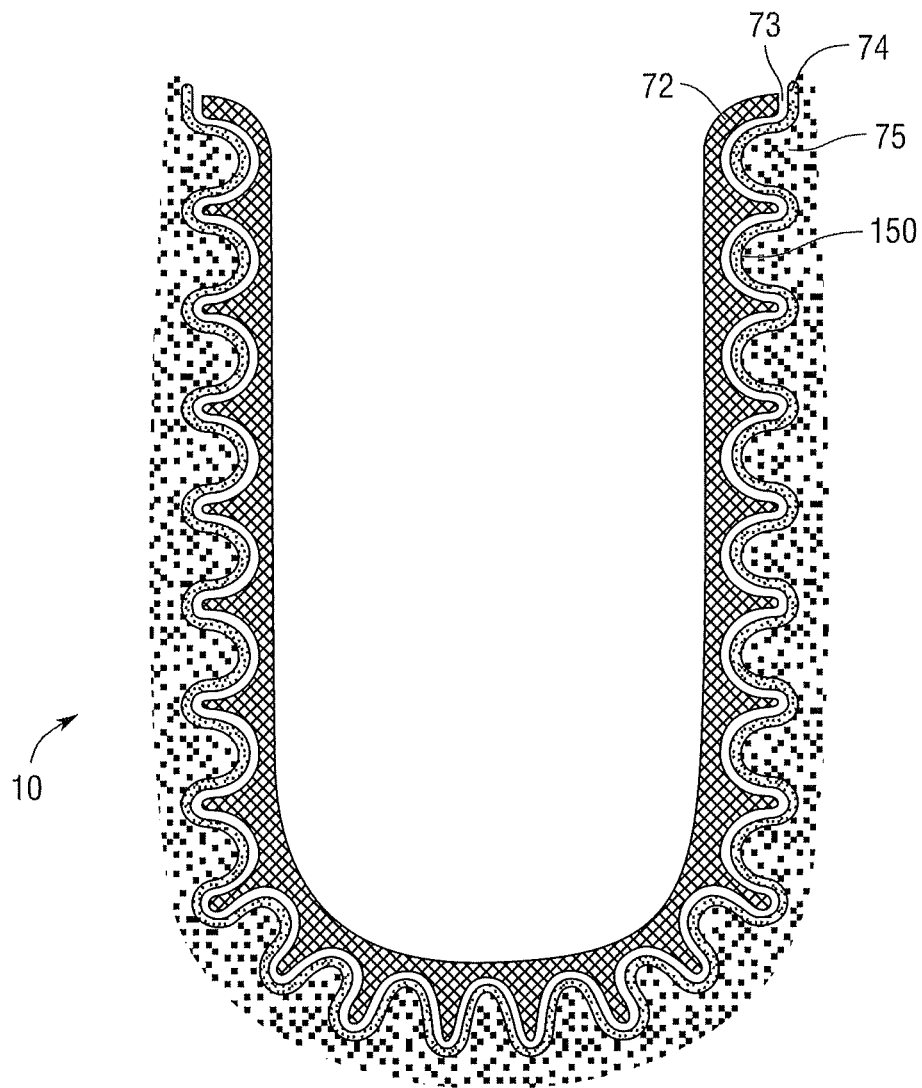
FIG. 18 is a cross-section of another preferred embodiment of a prosthetic liner of the present disclosure comprising an internal cushioning layer, a thin tough hydrogel membrane, a perforated polymer supporting layer and an external spongy layer.

FIG. 18 shows a cross-section of another preferred embodiment of a prosthetic liner 10 of the present disclosure comprising an internal cushioning layer 72, a thin tough hydrogel membrane 73, a perforated polymer supporting layer 74 and an external spongy layer 75. As shown in FIG. 18, liner 10 preferably comprises an internal ribbed or pinnately lobed structure to increase the internal surface area of the internal thin tough hydrogel membrane 73. Preferably, internal projections 150 are circumferential and uniform around the inside of the liner 10. The pinnately lobed structure would be made of many small conical or egg shaped projections 150 equally spaced out to increase the surface area available for moisture permeability. The construction of liner 10 shown in FIG. 18 supports and enables the thin tough hydrogel membrane 73. Immediately adjacent to the membrane 73 is the perforated polymer supporting layer 74. This layer 74 is heavily perforated to prevent any resistance to flow of water or moisture through it. Its purpose is to provide a mechanically supportive layer to the thin and less stout hydrogel membrane 73. Additionally, the hydrogel layer 73 may be more interior or exterior to the device, either configuration would be possible. In addition, the internal cushioning layer 72 and the external spongy layer 75, while named differently they each may be made of the same material, an open cell foam, or they could be made of different porous materials. The open cell foam enables very little resistance to the flow of water and would even soak up and absorb water.

Figure 19:
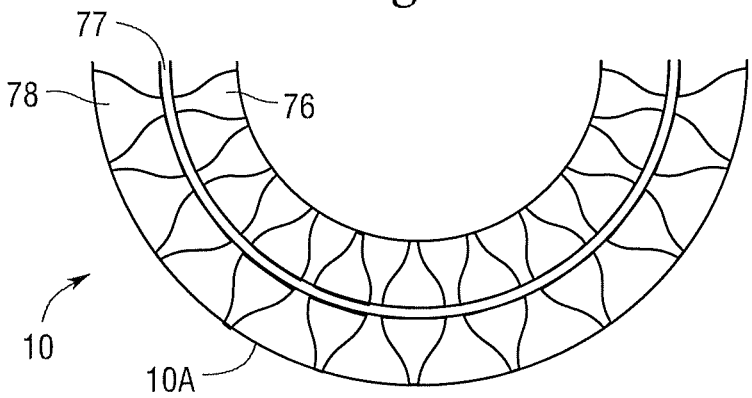
FIG. 19 shows another preferred embodiment of a liner of the present disclosure comprising two transmission layers sandwiching a hydrogel layer.

FIG. 19 shows another preferred embodiment of a liner 10 of the present disclosure comprising two transmission layers 76, 78 sandwiching a hydrogel layer 77. FIG. 19 is not to scale and has been enlarged for clarity. More specifically, FIG. 19 depicts a cross sectional view of a 3-dimensional hemispherical moisture permeable composite end cap 10A for a moisture permeable prosthetic limb liner 10. The two perforated elastomeric transmission layers 76, 78 preferably are similar to each other in that they contain the same profile for the pore that is going through them. This pore profile is that of a modified cone shape. The end of the pore that is exposed to the internal lumen of the hemisphere is very small. This pore then widens as it goes through the layer to terminate in a large opening that is on the side of the thin tough hydrogel membrane 77. On the opposite side of the hydrogel membrane the other layer the outer transmission layer 78 has the small pores terminating to the exterior of the hemispherical composite end cap 10A. In the outer transmission layer 78, the end of the pore terminating on the side of the internal membrane is the larger opening. End cap 10A may or may not include a wicking layer.

Figure 20A:
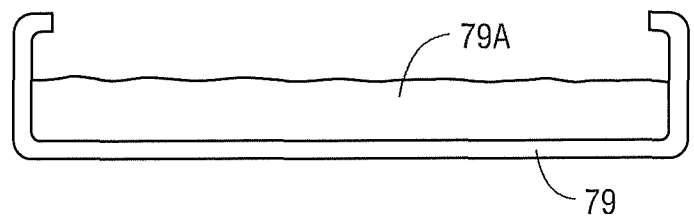
FIGS. 20A-20C schematically show a preferred multi-step method for manufacturing a thin tough hydrogel membrane of the present disclosure.
Figure 20B:
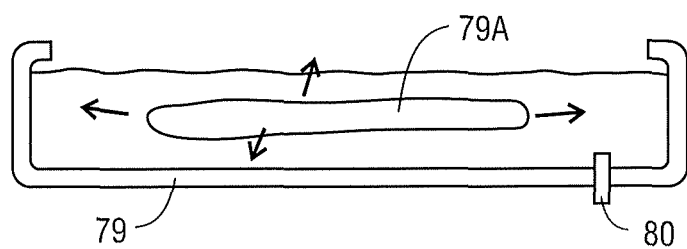
Figure 20C:
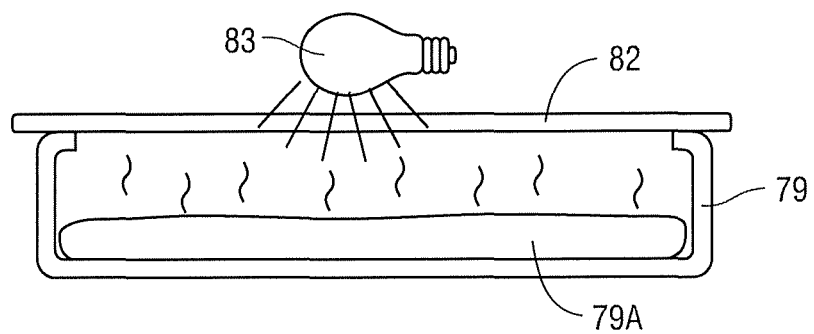

FIGS. 20A-20C schematically show a preferred multi-step method for manufacturing the thin tough hydrogel membranes for use in a liner 10 of the present disclosure. An important step of this method is the draining via draining pan 79 shown in FIG. 20B. Due to the extremely thin nature of the hydrogel membranes innovation was required to create a reliable method of manufacturing them. The major challenge in making the thin film hydrogels is that their precursor membranes are extremely fragile and prone to drying and shrinking and cracking, or swelling and breaking. Once the two step manufacture process is complete, the hydrogels are very resilient and tough, but until the last step of the process they need to be carefully handled and supported. The preferred method described herein is designed to reduce handling of the gels as much as possible throughout the manufacturing process. In a first step shown in FIG. 20A, the hydrogels 79A are cast in a tray 79 with a sealed bottom and sealed top, and sealed in the sides as well. The hydrogel 79A is cast by filling tray 79 with a first monomer solution. Tray 79 is transparent to UV light in the upper portion at least where the UV light can shine through to cure the first monomer solution into a hard gel 79A. The top plate is then removed and the hard gel 79A is trimmed. The edges are trimmed away from the edges of the tray 79. This is because of the swelling that results in the second stage of manufacture. Without trimming of the edges of the hard gel 79A, it will buckle and wrinkle as it attempts to spread out in the constrained environment of tray 79. After the gel 79A is trimmed, a secondary monomer solution is added to the same tray 79. The hard gel 79A is then allowed to soak in the second monomer solution under refrigeration and under agitation by a vibrating surface. Over the next 24 hours the gel 79A is allowed to come to osmotic equilibrium. After that period of time the tray 79 is drained through plug 80. The hard gel 79A sinks to the bottom as the solution is drained. A cover plate 82 is then returned to the tray 79 to cover hard gel 79A as shown in FIG. 20C and the UV light 83 is reapplied to cure the hard gel saturated with the second monomer solution into thin tough hydrogel 79A. This preferred method of making thin tough hydrogel 79A may be modified in various ways to alter the properties of the thin tough hydrogel, such as by adding nanoparticles, such as laponite or other materials.

EXAMPLE 1

L3_S3: Thin Tough Hydrogel Laponite Formulation (AMPS)=2-Acrylamido-2-methylpropanesulfonic acid
(MBAA)=N,N'-Methylenebis(acrylamide)
(AAm)=acrylamide
(NaCl)=Sodium Chloride
(K2S2O8)=Potassium Persulfate
Lanponite Content: 3 wt %
UV 1 Cook time: 6 hours
UV 2 Cook Time: 6 hours
Soak Time: 24 hours
Salt Concentration: 3 Molality in both networks
In this recipe for thin tough hydrogel the laponite was added into the first network. Preferably the laponite should insert itself between the polymers that form in the first step and not affect how the first network interacts with the 2nd network.
To Prepare Double Network Hydrogel: 1 mols AMPS
Preparation of First Network, AMPS W/Laponite
1) Mass out 15 g of Laponit.
2 Weigh out 0.5 Liter H20 (500.000 grams) and add to the Laponite, mix on stir plate for 30 minutes
3) While the laponite is mixing Weigh out 0.50 mol AMPS (103.624 grams)
4) Weigh out 0.02 mol MBAA (3.083 grams)
5) Weigh out 0.005 mol 2-oxoglutaric acid (0.073 grams)
6) Add MBAA, AMPS, and 2-oxoglutaric acid to the same bowl and grind with mortar and pastel until it is a fine powder
7) Add the MBAA, AMPS, 2-oxoglutric acid mixture to the dispersed laponite gels and mix for an hour
8) Add the Salt (87.66 grams) to this mixture and let it mix until it is fully dissolved
9) Measure out 0.75 g of Potassium Persulfate (Initiator) and add it to the solution
10) Pour solution into mold and irradiate for 6 hours
Preparation of Second Network, AAm
1) Weigh out 3 mol AAm (243.234 grams)
2) Weigh out 0.003 mol MBAA (0.462 grams)
3) Weigh out 0.001 mol potassium persulfate (0.270 grams)
4) Mix together in a bowl
5) Weigh out 1 L H20 (1000 grams)
6) Weigh out 3 mol of NaCl (175.32 g) and mix with water on stir plate till dissolved
7) Mix solution with AAm/MBAA/K2S2O8
7) Soak PAMPS membrane in this secondary AAm Solution 24 hours in a UV transparent tray
8) Drain tray and irradiate membrane with Ultra violet Light 6 hours
9) Rinse gel membrane continually using water pump for 2 days to remove unreacted material changing the water once daily.

FIGS. 21A and 21B schematically depict another preferred method of manufacturing a hydrogel membrane for use in a liner 10 of the present disclosure. FIGS. 21A and 21B show a curved dome shaped glass mold 84, 87 and a larger solid second mold half, 85, 88. The glass mold is designed to be transparent to UV light 86 so that the gel 79A can cure. A UV light 86 is placed into the glass mold 87 so that it can radially apply roughly equal UV energy in all directions. The gel 79A is formed between the glass bowl 87 and the larger mold half 88. These molds may be made using a variety of methods such as plaster, silicone casting, or 3d printing.

FIGS. 22A and 22B show a preferred embodiment of a thin tough hydrogel membrane 90 for a liner 10 according to the present disclosure. As shown in FIG. 22A, the moisture permeable hydrogel membrane 90 preferably is made in such a way as to have different densities and properties throughout its thickness. This is accomplished by having the percentages of water content greater on the outer sections 89 of the hydrogel gel membrane 90 and less in the center 91. For example, hydrogel membrane 90 may have 60% water content in the outer portions 89 and 30% water content in the internal core 91. These percentages are given only as an example and may not reflect the true desirable properties for maximal water penetration. Those numbers must be calculated for each application. FIG. 22B depicts various zones of properties that may be incorporated into a hydrogel membrane 90 at various sections thereof. In a hydrogel membrane 90 as shown in FIG. 22A having, for example, a thickness of 0.5 mm thin tough hydrogel material and about a 4 inch in diameter, various changes in properties from the outside to the inside maybe incorporated. For instance, for a given application the outer region 92, the water content may be set at 50% and in the center 93, the water content may be set at 95%. The higher the amount of water in the membrane the greater the rate of water permeation.

Figure 23A:
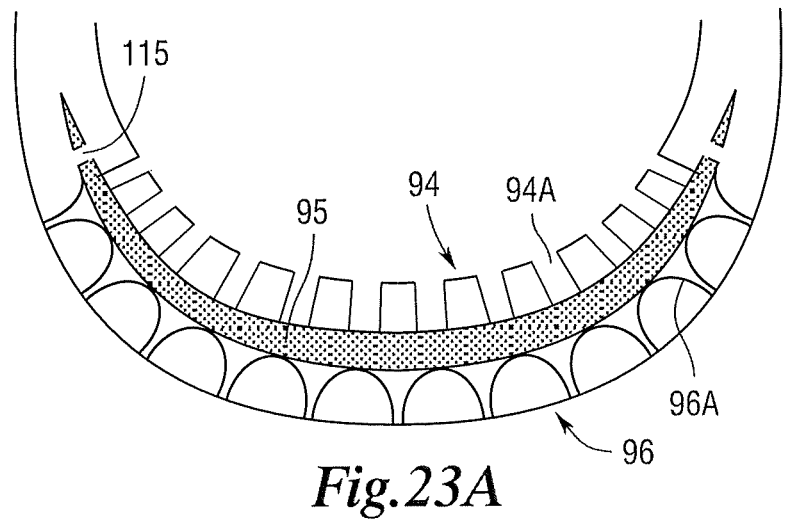
FIGS. 23A-23B show additional preferred embodiments of moisture permeable composites of the present disclosure comprising a three-layer design with a moisture permeable hydrogel membrane sandwiched by two polymer transmission layers.
Figure 23B:
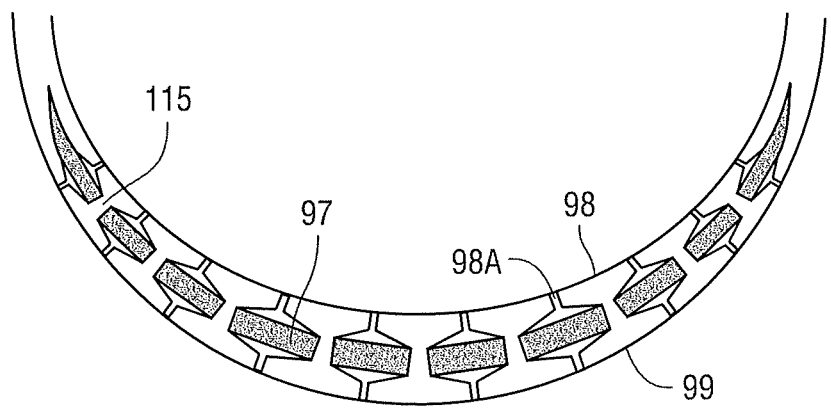

FIGS. 23A and 23B show additional preferred embodiments of moisture permeable composites useful in liners 10 of the present disclosure comprising a three-layer design with a moisture permeable hydrogel membrane 95, 97 sandwiched by two polymer transmission layers 94 and 96 or 98 and 99. FIG. 23A features an inner transmission layer 94 with a straight pore profile 94A. In FIG. 23A, the hydrogel layer 95 is shown having an exaggerated thickened for clarity and is not drawn to scale. Additionally, in the moisture permeable composite of FIG. 23A, the outer transmission layer 96 features a different pore profile than the inner transmission layer 94. It is a trumpet shape 96A. Each of the preferred embodiments shown in FIGS. 23A and 23B include use of a transmembrane locking pin 115. In FIG. 23A, the transmembrane locking pin 115 is disposed at the corners of the hydrogel membrane. The purpose of the locking pin is to keep the hydrogel layer 95 or 97 firmly in place and add to the anchoring effect of any glues or covalent bonding used. Preferably, hydrogel membranes 95, 97 do not become dislodged or become disordered.

The moisture permeable composite of FIG. 23B, preferably features a multitude of locking pins 115 throughout the entire area of the hydrogel membrane 97. Also, the profile of the pores 98A is a more radical valve shape which is the same in both inner and outer transmission layers 98 and 99.

Figure 24A:
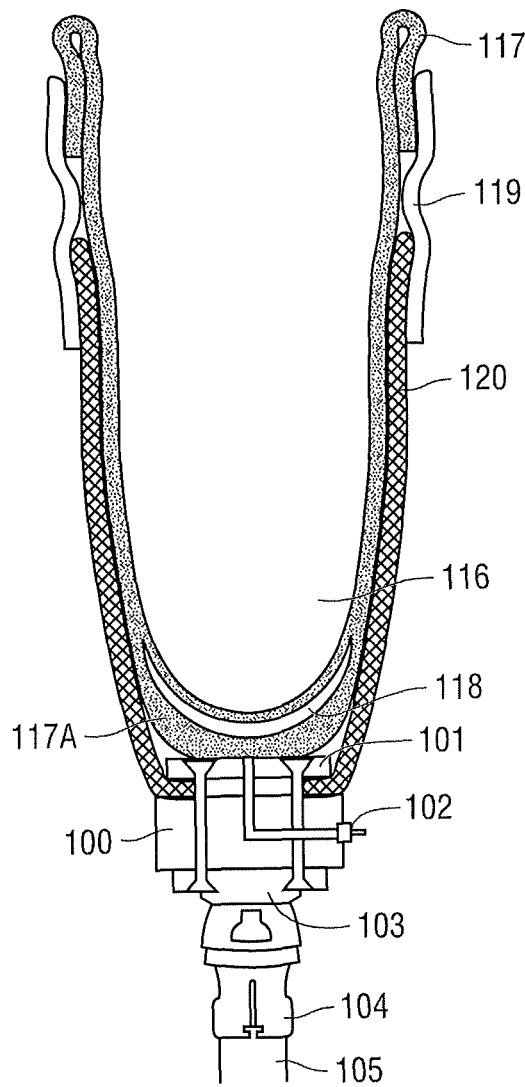
FIGS. 24A-24B illustrate how a moisture permeable prosthetic liner of the present disclosure fits into a prosthetic socket.
Figure 24B:
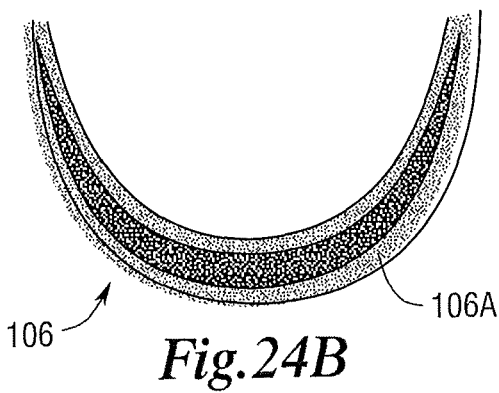

FIGS. 24A and 24B illustrate how the moisture permeable prosthetic liner 117 fits into the larger system of the prosthetic socket 120. At the center of FIG. 24 A is the residual limb 116. The residual limb 116 is a trans-tibial residual limb but can also be a trans-femoral as well or upper extremity. Immediately adjacent to the residual limb 116 is the moisture permeable prosthetic liner 117. In this particular embodiment the moisture permeable prosthetic liner features a hydrogel membrane 118 on the distal end. There are several parts of the socket which preferably may be needed to make the liner 117 function optimally. Part 100 is the vacuum pump. The vacuum pump 100 preferably is strong enough to maintain a range of about −25 inHg. Plate 101 affixes the vacuum pump 100 to the socket and preferably is made of steel, aluminum, titanium, alloy or other suitable material. Plate 101 is preferably placed on the interior of the socket and will make a bond to the interior of the socket. 103 is a pyramid adapter that allows the vacuum pump 100 to be linked to the pylon adapter 104 of pylon 105. Nozzle 102 is preferably present on the vacuum pump 100 to allow the channeling of moisture to a collection unit (not pictured) or dumped into the environment. Sealing sleeve 119 aids in preventing leakage between the liner 117 and the socket 120. FIG. 24B shows another preferred embodiment of the moisture permeable liner 106 having a smaller cushioning layer 106A on the bottom when compared to the thickness of the outer layer 117A of liner 117. The socket 120, the plate 101, the vacuum pump 100, and the pyramid adapter 103, preferably are all rigidly attached to one another with bolts or screws.

Figure 25A:
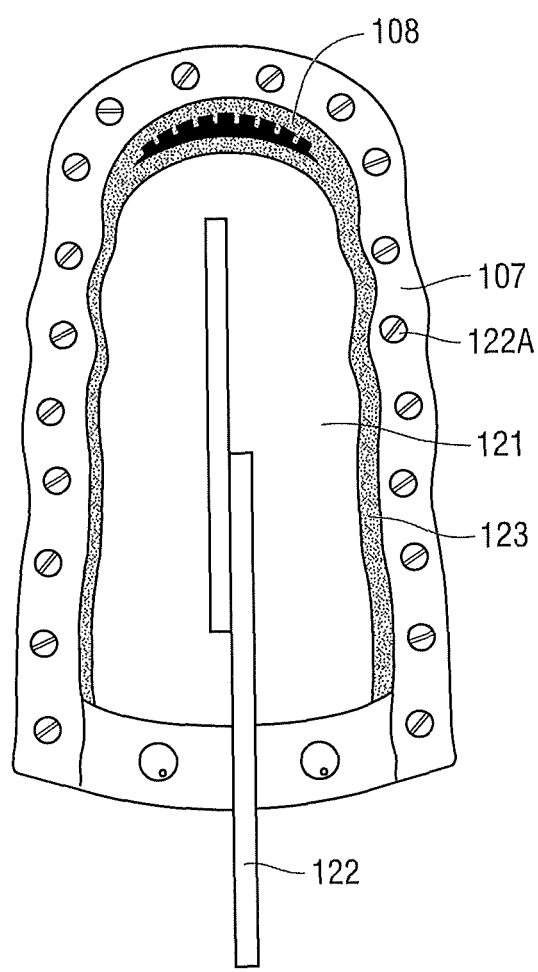
FIGS. 25A-25B schematically depict a preferred method of manufacturing a prosthetic liner of the present disclosure.
Figure 25B:
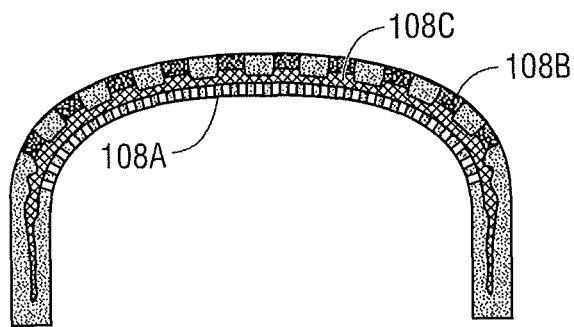

FIGS. 25A and 25B schematically depict a preferred method of manufacturing a prosthetic liner of the present disclosure. Such method employs a set of two steel poles 122, embedded into a plaster mold 121, and encased in a clear thermoplastic clamshell 107, held together with screws 122A. Between the clear clamshell 107 and the mold 121 is a space 123, which is filled with polymer material that forms the liner. The composite distal end 108, is embedded into the liner. Liner 108 is another preferred embodiment having very small pores 108A on the internal transmission layer. The outer transmission layer features large pores 108B. The inner hydrogel membrane 108C features an interlocking configuration designed to improve membrane stability within the composite without compromising the integrity of the membrane with perforations, similar to the use of locking pin 115 of FIGS. 23a and 23B.

Figure 26:
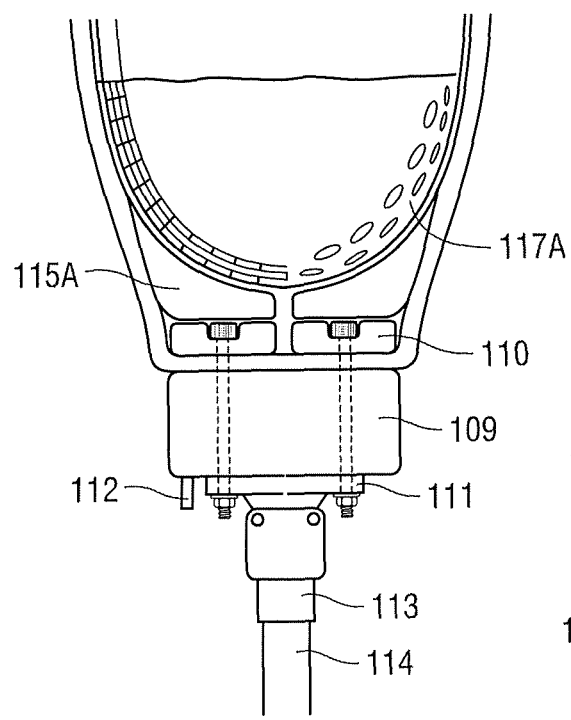
FIG. 26 shows a preferred embodiment of a prosthetic socket of the present disclosure having a spacer disposed between the flat part of the socket and the permeable liner.

FIG. 26 shows another preferred embodiment of a prosthetic socket 120A having a spacer 115A disposed between the flat part 110 and the permeable liner 117A. Spacer 115A preferably aids in the transmission of moisture away from the liner 117A as well as provide additional cushioning. Vacuum pump 109 corresponds to pump 100 in FIG. 24A. Nozzle 112 corresponds with nozzle 102 of FIG. 24A but is placed vertically facing down rather than horizontally outward. The pyramid adapter 111, the pylon adapter 113 and the pylon 11, correspond to 103, 104, and 105 of FIG. 24A, respectively. An important difference between the preferred embodiments of FIGS. 24A and 26 is the use of spacer 115A to provide cushioning to the thin liner 117A of FIG. 26. In FIG. 24A, liner 117 is thicker and provides its own cushioning eliminating the need for spacer 115A.

Figure 27:
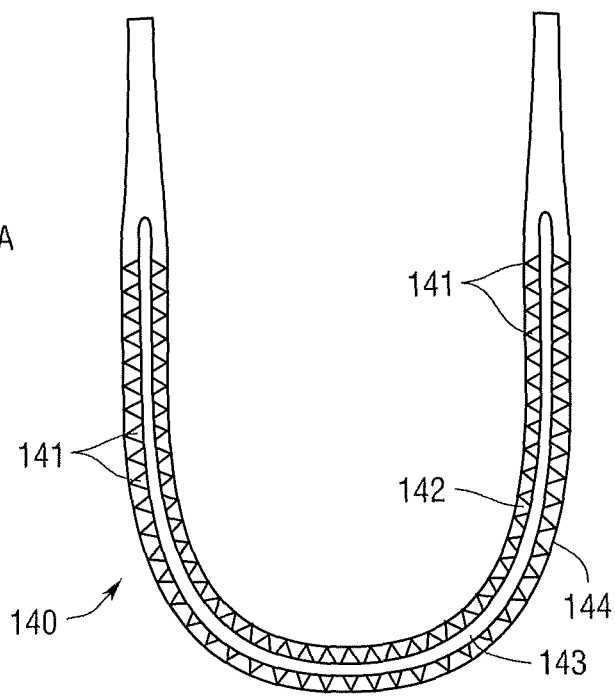
FIG. 27 shows a preferred prosthetic liner of the present disclosure having an elongated moisture permeable composite section.

FIG. 27 shows a preferred moisture permeable composite section 140, heretofore shown as a roughly hemispherical device affixed to the end of the largely homogeneous and tubular liner sleeve, as being extended along the length of the liner to encompass a greater surface area. The profile of the pores 141 shown is that of a triangle shaped profile which is meant to represent a 3 dimensional cone shape. In this preferred embodiment, there is a three-layer composite made of inner and outer porous elastomer layers 142 and 144 sandwiching a thin tough hydrogel membrane 143. Both inner and outer porous elastomer layers 142, 144 have the same profile of pore 141 formed into them. The main distinction of liner 140 is its elongated construction that provides an extended zone of moisture permeability to increase moisture removal from within a prosthetic socket according to the present disclosure.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A system for removing moisture from a residual limb inserted in a prosthesis comprising:
   a nonporous prosthesis socket;
   a liner disposed in the socket wherein the liner comprises a middle layer comprising a thin tough hydrogel membrane, a hydrogel or a dual network hydrogel; wherein the middle layer is convoluted for increased surface area; an inner layer comprising a porous elastomer or an open cell foam material; and an outer layer comprising a porous cushioning material;
   a nonporous seal that prevents air leakage from the space between the socket and the liner to the outside environment; and a vacuum source to reduce the pressure in the space between the socket and liner.

2. The system of claim 1 wherein the middle layer is disposed throughout the entire liner.

3. The system of claim 1 wherein the middle layer is disposed throughout only a portion and not the entirety of the liner.

* * * * *